US011648057B2

(12) United States Patent
Cook et al.

(10) Patent No.: US 11,648,057 B2
(45) Date of Patent: May 16, 2023

(54) OPTICAL ANALYZER ASSEMBLY WITH SAFETY SHUTDOWN SYSTEM FOR INTRAVASCULAR LITHOTRIPSY DEVICE

(71) Applicant: Bolt Medical, Inc., Carlsbad, CA (US)

(72) Inventors: Christopher A. Cook, Laguna Niguel, CA (US); Eric Schultheis, San Clemente, CA (US); Rachel Lynn Troutman, Carlsbad, CA (US); James Dee Swift, San Clemente, CA (US)

(73) Assignee: Bolt Medical, Inc., Carlsbad, CA (US)

( * ) Notice: Subject to any disclaimer, the term of this patent is extended or adjusted under 35 U.S.C. 154(b) by 0 days.

(21) Appl. No.: 17/736,894

(22) Filed: May 4, 2022

(65) Prior Publication Data

US 2022/0354578 A1   Nov. 10, 2022

Related U.S. Application Data

(60) Provisional application No. 63/186,391, filed on May 10, 2021.

(51) Int. Cl.
*A61B 18/24* (2006.01)
*A61B 18/26* (2006.01)
(Continued)

(52) U.S. Cl.
CPC .......... *A61B 18/245* (2013.01); *A61B 18/042* (2013.01); *A61B 18/26* (2013.01);
(Continued)

(58) Field of Classification Search
CPC ..... A61B 18/245; A61B 18/042; A61B 18/26; A61B 2018/00285; A61B 2018/2266; A61B 2018/2272
See application file for complete search history.

(56) References Cited

U.S. PATENT DOCUMENTS

| 4,649,924 A | 3/1987 | Faccardi |
|---|---|---|
| 4,699,147 A | 10/1987 | Chilson et al. |

(Continued)

FOREIGN PATENT DOCUMENTS

| AU | 2017205323 | 1/2022 |
|---|---|---|
| AU | 2019452180 | 1/2022 |

(Continued)

OTHER PUBLICATIONS

International Search Report and Written Opinion dated Jun. 28, 2022, in PCT Application Serial No. PCT/US2022/015577.

(Continued)

*Primary Examiner* — Brian T Gedeon
*Assistant Examiner* — Joshua Andrew Schum-Houck
(74) *Attorney, Agent, or Firm* — Roeder & Broder LLP; James P. Broder

(57) ABSTRACT

A catheter system for treating a treatment site within or adjacent to a vessel wall or a heart valve, includes a light source, a balloon, a light guide and an optical analyzer assembly. The light source generates first light energy. The balloon is positionable substantially adjacent to the treatment site. The balloon has a balloon wall that defines a balloon interior that receives a balloon fluid. The light guide receives the first light energy and guides the first light energy in a first direction from a guide proximal end toward a guide distal end positioned within the balloon interior. The optical analyzer assembly optically analyzes a second light energy from the light guide that moves in a second direction that is opposite the first direction. The optical analyzer assembly includes a safety shutdown system to inhibit the first light energy from being received by the guide proximal end of the light guide.

20 Claims, 8 Drawing Sheets

(51) Int. Cl.
  *A61B 18/04*     (2006.01)
  *A61B 18/00*     (2006.01)
  *A61B 18/22*     (2006.01)
(52) U.S. Cl.
  CPC .............. *A61B 2018/00285* (2013.01); *A61B 2018/2266* (2013.01); *A61B 2018/2272* (2013.01)

(56) References Cited

U.S. PATENT DOCUMENTS

| | | | |
|---|---|---|---|
| 4,799,479 A | 1/1989 | Spears | |
| 4,913,142 A | 4/1990 | Kittrell et al. | |
| 4,955,895 A | 9/1990 | Suglyama | |
| 4,960,108 A | 10/1990 | Reichel et al. | |
| 4,994,059 A | 2/1991 | Kosa et al. | |
| 5,034,010 A | 7/1991 | Kittrell et al. | |
| 5,041,121 A | 8/1991 | Wondrazek et al. | |
| 5,104,391 A | 4/1992 | Ingle | |
| 5,116,227 A | 5/1992 | Levy | |
| 5,152,768 A | 10/1992 | Bhatta | |
| 5,173,049 A | 12/1992 | Levy | |
| 5,181,921 A | 1/1993 | Makita et al. | |
| 5,200,838 A | 4/1993 | Nudelman | |
| 5,290,277 A | 3/1994 | Vercimak et al. | |
| 5,372,138 A | 12/1994 | Crowley | |
| 5,400,428 A | 3/1995 | Grace | |
| 5,422,926 A | 6/1995 | Smith | |
| 5,454,809 A | 10/1995 | Janssen | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,697,377 A | 12/1997 | Wittkamph | |
| 5,718,241 A | 2/1998 | Ben-Haim et al. | |
| 5,729,583 A | 3/1998 | Tang | |
| 5,772,609 A | 6/1998 | Nguyen et al. | |
| 5,891,135 A | 4/1999 | Jackson et al. | |
| 5,906,611 A | 5/1999 | Dodick et al. | |
| 5,944,697 A | 8/1999 | Benett et al. | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,368,318 B1 | 4/2002 | Visuri et al. | |
| 6,500,174 B1 | 12/2002 | Maguire et al. | |
| 6,514,203 B2 | 2/2003 | Bukshpan | |
| 6,514,249 B1 | 2/2003 | Maguire | |
| 6,524,251 B2 | 3/2003 | Rabiner et al. | |
| 6,538,739 B1 | 3/2003 | Visuri et al. | |
| 6,607,502 B1 | 8/2003 | Maguire et al. | |
| 6,652,547 B2 | 11/2003 | Rabiner et al. | |
| 6,666,834 B2 | 12/2003 | Restle et al. | |
| 6,773,447 B2 | 8/2004 | Laguna | |
| 6,849,994 B1 | 2/2005 | White et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,309,324 B2 | 12/2007 | Hayes et al. | |
| 7,470,240 B2 | 12/2008 | Schultheiss et al. | |
| 7,569,032 B2 | 8/2009 | Naimark et al. | |
| 7,599,588 B2 | 10/2009 | Eberle et al. | |
| 7,713,260 B2 | 5/2010 | Lessard | |
| 7,758,572 B2 | 7/2010 | Weber et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,972,299 B2 | 7/2011 | Carter | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,192,368 B2 | 6/2012 | Woodruff | |
| 8,292,913 B2 | 10/2012 | Warnack | |
| 8,364,235 B2 | 1/2013 | Kordis et al. | |
| 8,419,613 B2 | 4/2013 | Saadat | |
| 8,439,890 B2 | 5/2013 | Beyar | |
| 8,556,813 B2 | 10/2013 | Cashman et al. | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,817 B2 | 3/2015 | Starnberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,132 B2 | 3/2016 | Ghaffari et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,730,715 B2 | 8/2017 | Adams | |
| 9,764,142 B2 | 9/2017 | Imran | |
| 9,814,476 B2 | 11/2017 | Adams et al. | |
| 9,861,377 B2 | 1/2018 | Mantell et al. | |
| 9,867,629 B2 | 1/2018 | Hawkins et al. | |
| 9,894,756 B2 | 2/2018 | Weinkam et al. | |
| 9,955,946 B2 | 5/2018 | Miller et al. | |
| 9,974,963 B2 | 5/2018 | Imran | |
| 9,974,970 B2 | 5/2018 | Nuta | |
| 9,993,292 B2 | 6/2018 | Adams et al. | |
| 10,039,561 B2 | 8/2018 | Adams et al. | |
| 10,136,829 B2 | 11/2018 | Deno et al. | |
| 10,149,690 B2 | 12/2018 | Hawkins et al. | |
| 10,159,505 B2 | 12/2018 | Hakala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,357,264 B2 | 7/2019 | Kat-Kuoy | |
| 10,405,923 B2 | 9/2019 | Yu et al. | |
| 10,406,031 B2 | 9/2019 | Thyzel | |
| 10,420,569 B2 | 9/2019 | Adams | |
| 10,441,300 B2 | 10/2019 | Hawkins | |
| 10,478,202 B2 | 11/2019 | Adams et al. | |
| 10,517,620 B2 | 12/2019 | Adams | |
| 10,517,621 B1 | 12/2019 | Hakala et al. | |
| 10,537,287 B2 | 1/2020 | Braido et al. | |
| 10,555,744 B2 | 2/2020 | Nguyen et al. | |
| 10,561,428 B2 | 2/2020 | Eggert et al. | |
| 10,646,240 B2 | 5/2020 | Betelia et al. | |
| 10,682,178 B2 | 6/2020 | Adams et al. | |
| 10,702,293 B2 | 7/2020 | Adams et al. | |

(56) References Cited

U.S. PATENT DOCUMENTS

| | | |
|---|---|---|
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1* | 4/2011 | Melsky ............... A61B 18/1492 606/15 |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0071715 A1 | 3/2012 | Beyar et al. |
| 2012/0071867 A1* | 3/2012 | Ryan .................... A61B 18/24 606/15 |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0157892 A1 | 6/2012 | Reitmajer et al. |
| 2012/0203255 A1 | 8/2012 | Hawkins et al. |
| 2012/0221013 A1* | 8/2012 | Hawkins ............ A61B 17/2202 606/128 |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0116714 A1 | 5/2013 | Adams et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0180069 A1 | 6/2014 | Millett |
| 2014/0180126 A1 | 6/2014 | Millett |
| 2014/0180134 A1 | 6/2014 | Hoseit |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2015/0005576 A1 | 1/2015 | Diodone et al. |
| 2015/0039002 A1 | 2/2015 | Hawkins |

(56) References Cited

U.S. PATENT DOCUMENTS

| | | |
|---|---|---|
| 2015/0073430 A1 | 3/2015 | Hakala et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0104933 A1 | 4/2019 | Stern |
| 2019/0175111 A1 | 6/2019 | Genereux et al. |
| 2019/0175300 A1 | 6/2019 | Hom |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0388002 A1 | 12/2019 | Bozsak et al. |
| 2019/0388110 A1 | 12/2019 | Nguyen et al. |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1* | 4/2020 | Bacher ............... A61F 9/00821 |
| 2020/0129195 A1 | 4/2020 | McGowan et al. |
| 2020/0129741 A1 | 4/2020 | Kawwas |
| 2020/0197019 A1 | 6/2020 | Harper |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |

(56) References Cited

FOREIGN PATENT DOCUMENTS

| | | |
|---|---|---|
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A1 | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 A2 | 1/2001 |
| WO | 20060066169 A2 | 1/2006 |
| WO | WO2009121017 | 10/2009 |
| WO | WO2009149321 A1 | 12/2009 |
| WO | 2010042653 A1 | 4/2010 |
| WO | WO2011094379 | 8/2011 |
| WO | 20110126580 A2 | 10/2011 |
| WO | WO2012025833 | 3/2012 |
| WO | WO20120052924 A1 | 4/2012 |
| WO | WO20120120495 A2 | 9/2012 |
| WO | WO2013119662 | 8/2013 |
| WO | 20130169807 A1 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021067563 | 4/2021 |
| WO | WO2021086571 A1 | 5/2021 |
| WO | WO2021096922 A1 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing. Oct. 2015. This reference was cited in a prior Information Disclosure Statement. However, the relevant date was missing. The date has now been added.).

Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).

(56) References Cited

OTHER PUBLICATIONS

Meng et al., "Accurate Recovery Of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Posterior conference in San Francisco, May 8-11, 2019. (This reference was cited in a prior Information Disclosure Statement. However, the relevant date was missing. The date has now been added.).
Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
Schafter+Kirchhoff, Laser Beam Couplers series 60SMS for coupling into single-mode and polarization-maintaining fiber cables, Schafter+Kirchhoff, pp. 1-5, Germany.
Meng et al., "Accurate Recovery Of Atrial Endocardial Potential Maps From Non-contact Electrode Data." Auckland Bioengineering Institute. (ID 1421).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison Of Manual Vs Automatic Annotation To Identify Abnormal Substrate For Scar Related VT Ablation." LIRYC Institute, Bordeaux University Hospital, France (ID 1336).
International Search Report and Written Opinion dated April, 4, 2022 in PCT Application Serial No. PCT/US2021/062170.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion dated Nov. 8, 2022 in PCT Application Serial No. PCTUS/2022/039678.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Speclia: A Proof-of-Principle Study for Tissue-Specific Laser Surgery, Sensors, 2013, pp. 13717-13731, vol. 13, Basel, Switzeriand.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law 3ased on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.

(56) References Cited

OTHER PUBLICATIONS

Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett, 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, dated Jan. 16, 2019.
European Search Report, for European Patent Application No. 18185152.8, dated Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and On Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.

(56) References Cited

OTHER PUBLICATIONS

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions,Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

International Search Report and Written Opinion, PCT Application Serial No. PCT/US2022/047751 issued Feb. 10, 2023, by the European Patent Office.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

McAteer, James A., et al. "Ultracal-30 Gypsum Artificial Stones For Research On The Mechinisms Of Stone Breakage In Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland, NPL From 2015.

Medlight, "Cylindircal light diffuser Model RD", Medlight S.A., Switzerland, NPL from 2015.

Mayo, Michael E., "Interaction of Laser Radiation with Urinary Calculi", Cranfield University Defense and Security, PhD Thesis, 2009, Cranfield University.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'Nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing, NPL from 2015.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologies, 2014, Pinnacle Biologies, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

(56) References Cited

OTHER PUBLICATIONS

Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Fips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the EP/ISA, in PCT/US2021/048819, dated Jan. 14, 2022.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany, NPL From 2020.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044 2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421), NPL From 2019.
Oriel Instruments, "Introduction to Beam Splitters for Optical Research Applications", Apr. 2014, pp. 1-9, https://www.azoptics.com/Article.aspx?ArticalD=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated April, 4, 2022 in PCT Application Serial No. PCT/US2021/065073.

* cited by examiner

OPTICAL ANALYZER ASSEMBLY WITH SAFETY SHUTDOWN SYSTEM FOR INTRAVASCULAR LITHOTRIPSY DEVICE

RELATED APPLICATION

This application is related to and claims priority on U.S. Provisional Patent Application Ser. No. 63/186,391 filed on May 10, 2021, and entitled "OPTICAL ANALYZER ASSEMBLY WITH SAFETY SHUTDOWN SYSTEM FOR INTRAVASCULAR LITHOTRIPSY DEVICE". To the extent permissible, the contents of U.S. Application Ser. No. 63/186,391 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for treating a treatment site within or adjacent to a vessel wall or a heart valve. In various embodiments, the catheter system includes a light source, a balloon, a light guide and an optical analyzer assembly. The light source generates first light energy. The balloon is positionable substantially adjacent to the treatment site. The balloon has a balloon wall that defines a balloon interior that receives a balloon fluid. The light guide is configured to receive the first light energy at a guide proximal end and guide the first light energy in a first direction from the guide proximal end toward a guide distal end that is positioned within the balloon interior. The optical analyzer assembly is configured to optically analyze a second light energy from the light guide that moves in a second direction that is opposite the first direction. The optical analyzer assembly includes a safety shutdown system that is selectively activated to inhibit the first light energy from the light source from being received by the guide proximal end of the light guide.

In some embodiments, the catheter system further includes a pulse generator that is coupled to the light source. The pulse generator can be configured to trigger the light source to generate a source beam that is directed toward the light guide.

In certain embodiments, the safety shutdown system includes a safety interlock that is selectively activated to block the pulse generator from triggering the generation of the source beam with the light source.

In various embodiments, the safety shutdown system includes a shutter that is selectively activated to block the source beam from being directed toward the light guide.

In some embodiments, the first light energy induces generation of a plasma within the balloon interior.

In certain embodiments, the guide distal end includes a distal light receiver that receives the second light energy from within the balloon interior. The second light energy moves through the light guide in the second direction.

In some embodiments, the second light energy that is received by the distal light receiver is emitted from the plasma that is generated in the balloon fluid within the balloon interior.

In various embodiments, the second light energy that is received by the distal light receiver is optically analyzed by the optical analyzer assembly.

In some embodiments, the optical analyzer assembly is configured to optically determine whether or not plasma generation within the balloon interior has occurred within the balloon interior.

In certain embodiments, the optical analyzer assembly is configured to optically detect a failure of the light guide between the guide proximal end and the guide distal end.

In some embodiments, the optical analyzer assembly is configured to optically detect potential damage to the light guide at any point along a length of the light guide from the guide proximal end to the guide distal end.

In certain embodiments, the optical analyzer assembly includes a beamsplitter and a photodetector, the beamsplitter being configured to receive the second light energy and direct a portion of the second light energy to the photodetector.

In some embodiments, the optical analyzer assembly further includes an optical element that is positioned along a beam path between the beamsplitter and the photodetector, the optical element being configured to couple the portion of the second light energy to the photodetector.

In certain embodiments, the optical analyzer assembly can further include a second beamsplitter that is positioned along the beam path between the beamsplitter and the photodetector, the second beamsplitter being configured to receive the second light energy and direct at least a portion of the second light energy to the photodetector.

In some embodiments, the photodetector generates a signal based at least in part on visible light that is included with the portion of the second light energy.

In certain embodiments, the signal from the photodetector is amplified with an amplifier to provide an amplified signal that is directed to control electronics to determine an intensity of the plasma generation within the balloon interior.

In some embodiments, the optical analyzer assembly includes a beamsplitter and an imaging device, the beamsplitter being configured to receive the second light energy and direct at least a portion of the second light energy to the imaging device.

In certain embodiments, the light source includes a laser.

In some embodiments, the light source includes an infrared laser that emits the first light energy in the form of pulses of infrared light.

In some embodiments, the light guide includes an optical fiber.

The present invention is further directed toward a method for treating a treatment site within or adjacent to a vessel wall or a heart valve, comprising the steps of generating first light energy with a light source; positioning a balloon substantially adjacent to the treatment site, the balloon having a balloon wall that defines a balloon interior, the balloon interior receiving a balloon fluid; receiving the first light energy at a guide proximal end of a light guide; guiding the first light energy in a first direction from the guide proximal end toward a guide distal end that is positioned within the balloon interior; and optically analyzing a second light energy from the light guide that moves in a second direction that is opposite the first direction, the optical analyzer assembly including a safety shutdown system that is selectively activated to inhibit the first light energy from the light source from being received by the guide proximal end of the light guide.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

As used herein, the terms "intravascular lesion", "vascular lesion" and "treatment site" are used interchangeably unless otherwise noted. The intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

Figure 1:
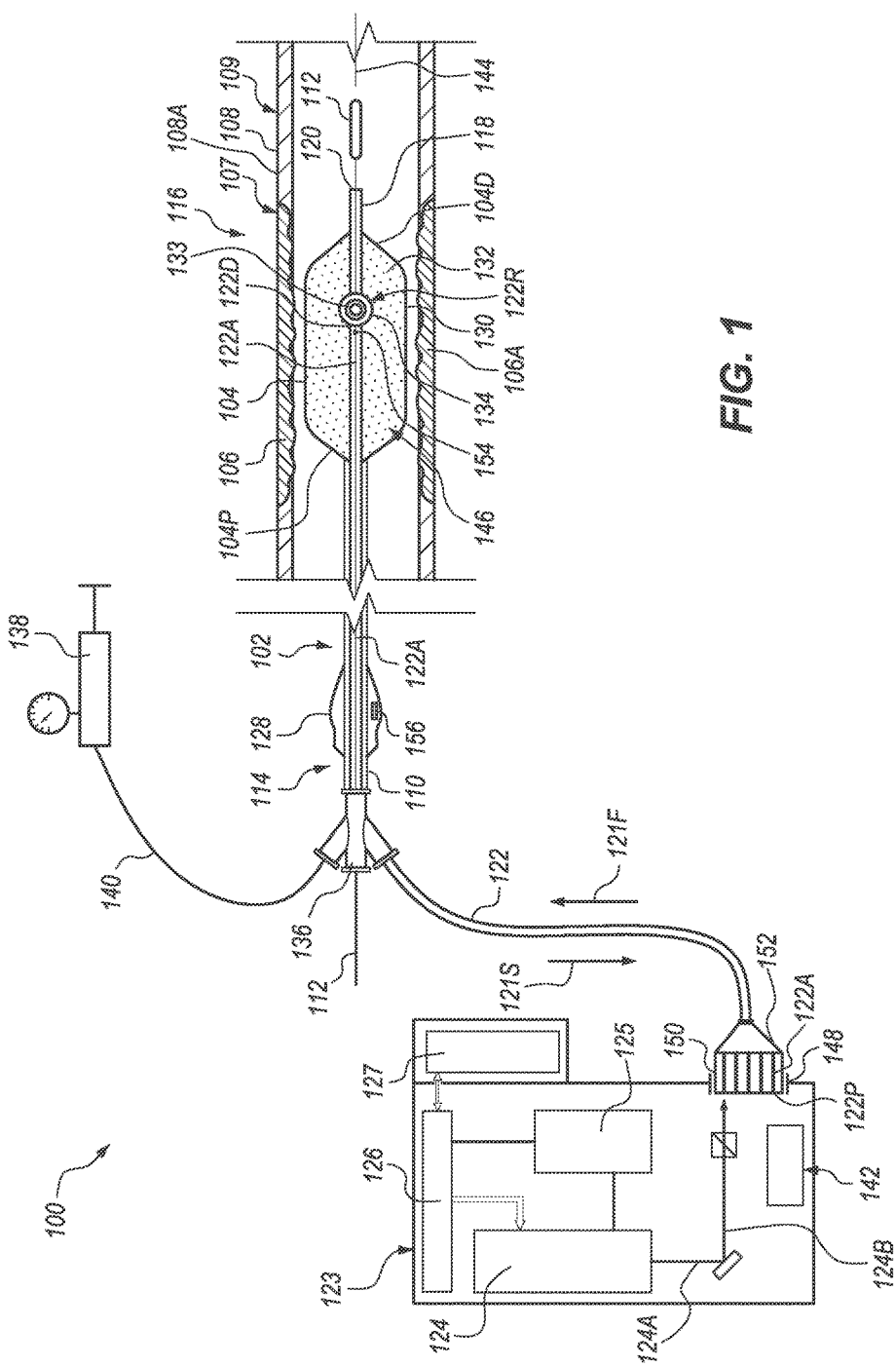
FIG. 1 is a schematic cross-sectional view of an embodiment of a catheter system in accordance with various embodiments herein, the catheter system including an optical analyzer assembly having features of the present invention.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more treatment sites within or adjacent a vessel wall of a blood vessel, or on or adjacent to a heart valve, within a body of a patient. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), a handle assembly 128, and an optical analyzer assembly 142. Alternatively, the catheter system 100 can include more components or fewer components than those specifically illustrated and described in relation to FIG. 1.

It is appreciated that while the catheter system 100 is generally described as including a light guide bundle 122 including one or more light guides 122A, and a light source 124, in some alternative embodiments, the catheter system 100 can include an energy guide bundle that includes different types of energy guides, and/or a different type of energy source.

In various embodiments, the catheter 102 is configured to move to a treatment site 106 within or adjacent to a vessel wall 108A of a blood vessel 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions. Still alternatively, in some implementations, the catheter 102 can be used at a treatment site 106 within or adjacent a heart valve within the body 107 of the patient 109.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a balloon fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106. It is appreciated that although FIG. 1 illustrates the balloon wall 130 of the balloon 104 being shown spaced apart from the treatment site 106 of the blood vessel 108 when in the inflated state, this is done merely for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloon 104 is made from silicone. In other embodiments, the balloon 104 can be made from polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloons 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluid 132 suitable for use herein is biocompatible. A volume of balloon fluid 132 can be tailored by the chosen light source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as perfluorocarbon dodecafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluid 132 can include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG—emission maximum=1064 nm) lasers, holmium:YAG (Ho:YAG—emission maximum=2.1 µm) lasers, or erbium:YAG (Er:YAG—emission maximum=2.94 µm) lasers. In some embodiments, the absorptive agents can be water soluble. In other embodiments, the absorptive agents are not water soluble. In some embodiments, the absorptive agents used in the balloon fluids 132 can be tailored to match the peak emission of the light source 124. Various light sources 124 having emission wavelengths of at least ten nanometers to one millimeter are discussed elsewhere herein.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. Each of the light guides 122A can have a guide distal end 122D that is at any suitable longitudinal position relative to a length of the balloon 104. In some embodiments, each light guide 122A can be an optical fiber and the light source 124 can be a laser. The light source 124 can be in optical communication with the light guides 122A at the proximal portion 114 of the catheter system 100. More particularly, the light source 124 can selectively, simultaneously, sequentially and/or alternatively be in optical communication with each of the light guides 122A in any desired combination, order and/or pattern.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, the light guides 122A can be disposed either uniformly or non-uniformly about the guidewire lumen 118 and/or the catheter shaft 110 to achieve the desired effect in the desired locations.

The catheter system 100 and/or the light guide bundle 122 can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A can have any suitable design for purposes of generating plasma and/or pressure waves in the balloon fluid 132 within the balloon interior 146. In certain embodiments, the light guides 122A can include an optical fiber or flexible light pipe. The light guides 122A can be thin and flexible and can allow light signals to be sent with very little loss of strength. The light guides 122A can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide first light energy along its length from a guide proximal end 122P toward the guide distal end 122D having at least one optical window (not shown) that is positioned within the balloon interior 146.

In various embodiments, the guide distal end 122D can further include and/or incorporate a distal light receiver 122R that enables second light energy to be moved back into and through the light guide 122A from the guide distal end 122D to the guide proximal end 122P. Stated another way, the first light energy can move in a first direction 121F along the light guide 122A that is generally from the guide proximal end 122P toward the guide distal end 122D of the light guide 122A. The second light energy, which in certain situations can comprise at least a portion of the first light energy, can move in a second direction 121S along the light guide 122A that is substantially opposite the first direction 121F, i.e. from the guide distal end 122D toward the guide proximal end 122P of the light guide 122A. Moreover, as described in greater detail herein below, the second light energy emitted from the guide proximal end 122P after being moved back through the light guide 122A (in the second direction 121S) can be separated and then optically detected, interrogated and/or analyzed through use of the optical analyzer assembly 142 in order to determine accurate operational modes, with both non-fault conditions and fault conditions, of the light guides 122A.

The light guides 122A can assume many configurations about and/or relative to the catheter shaft 110 of the catheter 102. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A can be disposed within one or more light guide lumens within the catheter shaft 110.

The light guides 122A can also be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the light guides 122A can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. The photoacoustic transducers 154 can have a shape that corresponds with and/or conforms to the guide distal end 122D of the light guide 122A.

The photoacoustic transducer 154 is configured to convert first light energy into an acoustic wave at or near the guide distal end 122D of the light guide 122A. The direction of the acoustic wave can be tailored by changing an angle of the guide distal end 122D of the light guide 122A.

In certain embodiments, the photoacoustic transducers 154 disposed at the guide distal end 122D of the light guide 122A can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The light guide 122A can further include additional photoacoustic transducers 154 disposed along one or more side surfaces of the length of the light guide 122A.

In some embodiments, the light guides 122A can further include one or more diverting features or "diverters" (not shown in FIG. 1) within the light guide 122A that are configured to direct light to exit the light guide 122A toward a side surface which can be located at or near the guide distal end 122D of the light guide 122A, and toward the balloon wall 130. A diverting feature can include any feature of the system that diverts first light energy from the light guide 122A away from its axial path toward a side surface of the light guide 122A. The light guides 122A can each include one or more light windows disposed along the longitudinal or circumferential surfaces of each light guide 122A and in optical communication with a diverting feature. Stated in another manner, the diverting features can be configured to direct first light energy in the light guide 122A toward a side surface that is at or near the guide distal end 122D, where the side surface is in optical communication with a light window. The light windows can include a portion of the light guide 122A that allows first light energy to exit the light guide 122A from within the light guide 122A, such as a portion of the light guide 122A lacking a cladding material on or about the light guide 122A.

Examples of the diverting features suitable for use include a reflecting element, a refracting element, and a fiber diffuser. The diverting features suitable for focusing first light energy away from the tip of the light guides 122A can include, but are not to be limited to, those having a convex surface, a gradient-index (GRIN) lens, and a mirror focus lens. Upon contact with the diverting feature, the first light energy is diverted within the light guide 122A to one or more of a plasma generator 133 and the photoacoustic transducer 154 that is in optical communication with a side surface of the light guide 122A. As noted, the photoacoustic transducer 154 then converts first light energy into an acoustic wave that extends away from the side surface of the light guide 122A.

The source manifold 136 can be positioned at or near the proximal portion 114 of the catheter system 100. The source manifold 136 can include one or more proximal end openings that can receive the one or more light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132 as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

As illustrated in FIG. 1, in certain embodiments, at least a portion of the optical analyzer assembly 142 can also be positioned substantially within the system console 123. Alternatively, components of the optical analyzer assembly 142 can be positioned in a different manner than what is specifically shown in FIG. 1.

As shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, such as the guide proximal end 122P, of each of the light guides 122A. The guide coupling housing 150 is configured to fit and be selectively retained within the console connection aperture 148 to provide the mechanical coupling between the light guide bundle 122 and the system console 123.

The light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

The light source 124 can be selectively and/or alternatively coupled in optical communication with each of the light guides 122A, such as to the guide proximal end 122P of each of the light guides 122A, in the light guide bundle 122. In particular, the light source 124 is configured to generate first light energy in the form of a source beam 124A, such as a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, the light source 124 can be configured to provide sub-millisecond pulses of first light energy from the light source 124 that are focused onto a small spot in order to couple it into the guide proximal end 122P of the light guide 122A. Such pulses of first light energy are then directed and/or guided along the light guides 122A to a location within the balloon interior 146 of the balloon 104, thereby inducing plasma formation (also sometimes referred to herein as a "plasma flash") in the balloon fluid 132 within the balloon interior 146 of the balloon 104, such as via the plasma generator 133 that can be located at or near the guide distal end 122D of the light guide 122A. In particular, the light emitted at the guide distal end 122D of the light guide 122A is directed toward and energizes the plasma generator 133 to form the plasma within the balloon fluid 132 within the balloon interior 146. The plasma formation causes rapid bubble formation, and imparts pressure waves upon the treatment site 106. An exemplary plasma-induced bubble 134 is illustrated in FIG. 1.

When the plasma initially forms in the balloon fluid 132 within the balloon interior 146, it emits broad-spectrum electromagnetic radiation. This can be seen as a flash of broad spectrum light detectable by the naked eye. A portion of the light emitted from the plasma bubble 134, in the form of the second light energy, can be coupled into the distal light receiver 122R at the guide distal end 122D of the light guide 122A and travel back to the guide proximal end 122P where it can be separated, detected and analyzed through use of the optical analyzer assembly 142. The intensity and timing of the visible light pulse relative to the plasma generating pulse provides an indication that the plasma generator 133 functioned, its energy output and its functional or operational condition. Visible light flashes may occur in other locations of the light guide 122A if the light guide 122A is damaged or broken. Such other visible light flashes will also be coupled into the light guide 122A and carried back to the guide proximal end 122P. The intensity and timing of these other light pulses provide an indication of damage to or failure of the light guide 122A or the plasma generator 133. In such situations, the optical analyzer assembly 142 can include a safety shutdown system 283 (illustrated in FIG. 2A) that can be selectively activated to shut down operation of the catheter system 100.

In various implementations of the optical analyzer assembly 142, the optical analyzer assembly 142 can be configured to detect certain functional or operational conditions of the light guide 122A and/or the plasma generator 133, as are further illustrated in FIGS. 3A-3F, such as (i) normal operation conditions; (ii) intermittent gas bubble production conditions; (iii) guide distal end plasma initiation conditions; (iv) housing/target failure conditions; (v) broken light guide (fiber) conditions, such as from broken light guides at the guide distal end; and (vi) chewback conditions, such as from broken light guides along the light guide and at least somewhat spaced apart from the guide distal end. It is appreciated that some identified operation conditions, including normal operation conditions, intermittent gas bubble production conditions, and guide distal end plasma initiation conditions, although they may require further monitoring of the condition of the light guide 122A and/or the plasma generator 133, do not require immediate stopping of operation of the catheter system 100 or replacement of the light guide 122A and/or the plasma generator 133. However, it is further appreciated that other identified operation conditions, such as housing/target failure conditions, broken light guide (fiber) conditions, and chewback conditions, may and often do require stopping of operation of the catheter system 100 and replacement of the light guide 122A and/or the plasma generator 133.

The configuration of the plasma generator 133 and/or the distal light receiver 122R further allows ambient light that originates outside of the catheter 102 to be coupled into the guide distal end 122D of the light guide 122A. In one implementation, the optical analyzer assembly 142 monitors for returned ambient light energy that traverses the light guide 122A from the guide distal end 122D to the guide proximal end 122P. If any ambient light energy is present and detected by the optical analyzer assembly 142 in such situations, this is an indication that the catheter 102 is located outside of the body 107 of the patient 109, and the optical analyzer assembly 142 can be configured to lock out the light source 124 accordingly. In particular, in such situations, the safety shutdown system 283 of the optical analyzer assembly 142 can be selectively activated to shut down operation of the catheter system 100.

In various non-exclusive alternative embodiments, the sub-millisecond pulses of first light energy from the light source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of first light energy can be delivered to the treatment site 106 at a frequency that can be greater than 5000 Hz or less than one Hz, or any other suitable range of frequencies.

It is appreciated that although the light source 124 is typically utilized to provide pulses of first light energy, the light source 124 can still be described as providing a single source beam 124A, i.e. a single pulsed source beam.

The light sources 124 suitable for use can include various types of light sources including lasers and lamps. For example, in certain non-exclusive embodiments, the light source 124 can be an infrared laser that emits first light energy in the form of pulses of infrared light. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the light sources 124 suitable for use in the catheter system 100 can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In various non-exclusive alternative embodiments, the catheter system 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm extending radially from the light guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the light guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the light source 124, the system controller 126, the GUI 127, the handle assembly 128, and the optical analyzer assembly 142. The power source 125 can have any suitable design for such purposes.

The system controller 126 is electrically coupled to and receives power from the power source 125. The system controller 126 is coupled to and is configured to control operation of each of the light source 124, the GUI 127 and the optical analyzer assembly 142. The system controller 126 can include one or more processors or circuits for purposes of controlling the operation of at least the light source 124, the GUI 127 and the optical analyzer assembly 142. For example, the system controller 126 can control the light source 124 for generating pulses of first light energy as desired and/or at any desired firing rate. The system controller 126 can control and/or operate in conjunction with the optical analyzer assembly 142 to effectively provide real-time continuous monitoring of the performance, reliability, safety and proper usage of the catheter system 100.

The system controller 126 can further be configured to control operation of other components of the catheter system 100 such as the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. The GUI 127 is electrically connected to the system controller 126. With such design, the GUI 127 can be used by the user or operator to ensure that the catheter system 100 is effectively utilized to impart pressure onto and induce fractures at the treatment site(s) 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127 and the optical analyzer assembly 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. In some embodiments, the circuitry 156 can receive electrical signals or data from the optical analyzer assembly 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, such as within the system console 123. It is understood that the handle assembly 128 can include fewer or additional components than those specifically illustrated and described herein.

As an overview, and as provided in greater detail herein, the optical analyzer assembly 142 is configured to effectively monitor the performance, reliability, safety and proper usage of the catheter system 100. During use of the catheter system 100, when the plasma initially forms in the balloon fluid 132 within the balloon interior 146, as a result of a pulse of the first light energy being directed into the balloon fluid 132 within the balloon interior 146, the plasma flash emits broad-spectrum electromagnetic radiation. The plasma flash can be effectively captured in the form of a flash signature (or flash signal) that can include summary parameters such as a pulse maximum value, rise time, width, and start time relative to a reference, as well as including a measure of signal volatility (described as a number of transitions), all of which can provide indications of the condition of the light guide 122A and/or the plasma generator 133.

At least a portion of the first light energy emitted can reflect off of, or otherwise be received by, the distal light receiver 122R near the guide distal end 122D of the light guide 122A. Such portion of the first light energy can thus travel back through the light guide 122A as second light energy that moves in the second direction 121S to the guide proximal end 122P where it can be separated, detected and analyzed through use of the optical analyzer assembly 142. The intensity and timing of the visible light pulse relative to the plasma-generating pulse from the light source 124 provides an indication that the plasma generator 133 functioned, its energy output, and its functional condition. It is appreciated that visible light flashes may occur in other locations along the length of the light guide 122A if the light guide 122A is damaged or broken. Such additional light flashes will also be coupled into the light guide 122A and carried back in the second direction 121S to the guide proximal end 122P. The intensity and timing of these additional light pulses can indicate a damaged light guide 122A or plasma generator 133.

By evaluating and/or analyzing the intensity and timing of the visible light pulse relative to the plasma-generating pulse from the light source 124, the optical analyzer assembly 142 is able to identify operational conditions of the light guide 122A and/or the plasma generator 133 such as (i) normal operation conditions, where plasma is generated substantially directly adjacent to the plasma generator 133 when the first light energy is directed from the guide distal end 122D of the light guide 122A toward the plasma generator 133 and thus impinges on a target surface of the plasma generator 133; (ii) intermittent gas bubble production conditions, where gas bubbles formed within the balloon fluid 132 are found between the guide distal end 122D of the light guide 122A and the plasma generator 133 that optically impact the directing of the first light energy toward the target surface of the plasma generator 133; (iii) guide distal end plasma initiation conditions, where there may be some debris substantially adjacent to the guide distal end 122D of the light guide 122A which causes plasma to be generated at such point substantially adjacent to the guide distal end 122D of the light guide 122A rather than substantially directly adjacent to the plasma generator 133; (iv) housing/target failure conditions, where there is a failure to generate the desired plasma flash in the balloon fluid 132 within the balloon interior 146 due to issues or problems with the light guide 122A and/or the plasma generator 133; (v) broken light guide (fiber) conditions, such as broken light guides 122A at the guide distal end 122D, where little or no plasma is generated in the balloon fluid 132 within the balloon interior 146, and any minimal plasma that may be generated has a lower pulse maximum value due to the first light energy being directed in multiple disparate directions away from the guide distal end 122D of the light guide 122A rather than just directly toward the plasma generator 133; and (vi) chewback conditions, such as broken light guides 122A along the length of the light guide 122A and at least somewhat spaced apart from the guide distal end 122D, where plasma generation can occur in the balloon fluid 132 within the balloon interior 146 substantially adjacent to where a break may exist along the length of the light guide 122A. It is appreciated that some of these identified operation conditions, including normal operation conditions, intermittent gas bubble production conditions, and guide distal end plasma initiation conditions, although they may require further monitoring of the condition of the light guide 122A and/or the plasma generator 133, do not require immediate stopping of operation of the catheter system 100 or replacement of the light guide 122A and/or the plasma generator 133. However, it is further appreciated that other identified operation conditions, such as housing/target failure conditions, broken light guide (fiber) conditions, and chewback conditions, may and often do require stopping of operation of the catheter system 100 and replacement of the light guide 122A and/or the plasma generator 133.

It is appreciated that the misuse or failure of an energy-driven plasma generator 133 or associated light guide 122A, such as if the light guide 122A and/or the catheter system 100 is used outside the body 107 of the patient 109 and/or if the light guide 122A breaks or is damaged during the use of the catheter system 100, could lead to patient or operator harm resulting from the leaked energy. Potential harms include tissue burns and retinal damage. As noted above, in some embodiments, the light source 124 is a laser that emits invisible infrared light, making visible detection by the operator impossible. Thus, if the optical analyzer assembly 142 indicates any such misuse or failures to have occurred, the procedure and energy delivery, such as laser energy delivery, must be stopped immediately to mitigate the associated risks to the patient and the operator. Stated in another manner, with the design of the optical analyzer assembly 142 described herein, the present invention detects any noted misuses or failures within the catheter system 100, such as misuse of the catheter system 100 and/or breaking of, damage to, or failure of the light guide 122A and/or the plasma generator 133, and provides an indicator or signal that the system controller 126 can use to lock out the light source 124. In certain embodiments, the locking out of the light source 124 can be accomplished through use of the safety shutdown system 283, which in some such embodiments can include one or more of a safety interlock 284 (illustrated in FIG. 2A) and a shutter 286 (illustrated in FIG. 2A), that can be incorporated as part of the optical analyzer assembly 142. This provides a necessary safety interlock and mitigation for a potentially hazardous condition in which the light source 124 can leak out of any part of the catheter system 100 or light guide 122A due to misuse or failure. Moreover, the system controller 126 could be used to indicate to the surgeon, such as via the GUI 127, to halt the procedure and remove the catheter 102 from the patient 109 under treatment. A simple example of potential misuse would be attempting to energize the catheter system 100 when it is outside of the body 107 of the patient 109 and/or away from the intended treatment site 106. The emitted energy could unintentionally be viewed by the operator resulting in retinal damage.

It is further appreciated that the optical analyzer assembly 142 can have any suitable design for purposes of effectively monitoring the safety, performance, reliability and proper usage of the catheter system 100. Certain non-exclusive examples of potential designs and applications for the optical analyzer assembly 142 are described in detail herein below.

Figure 2A:
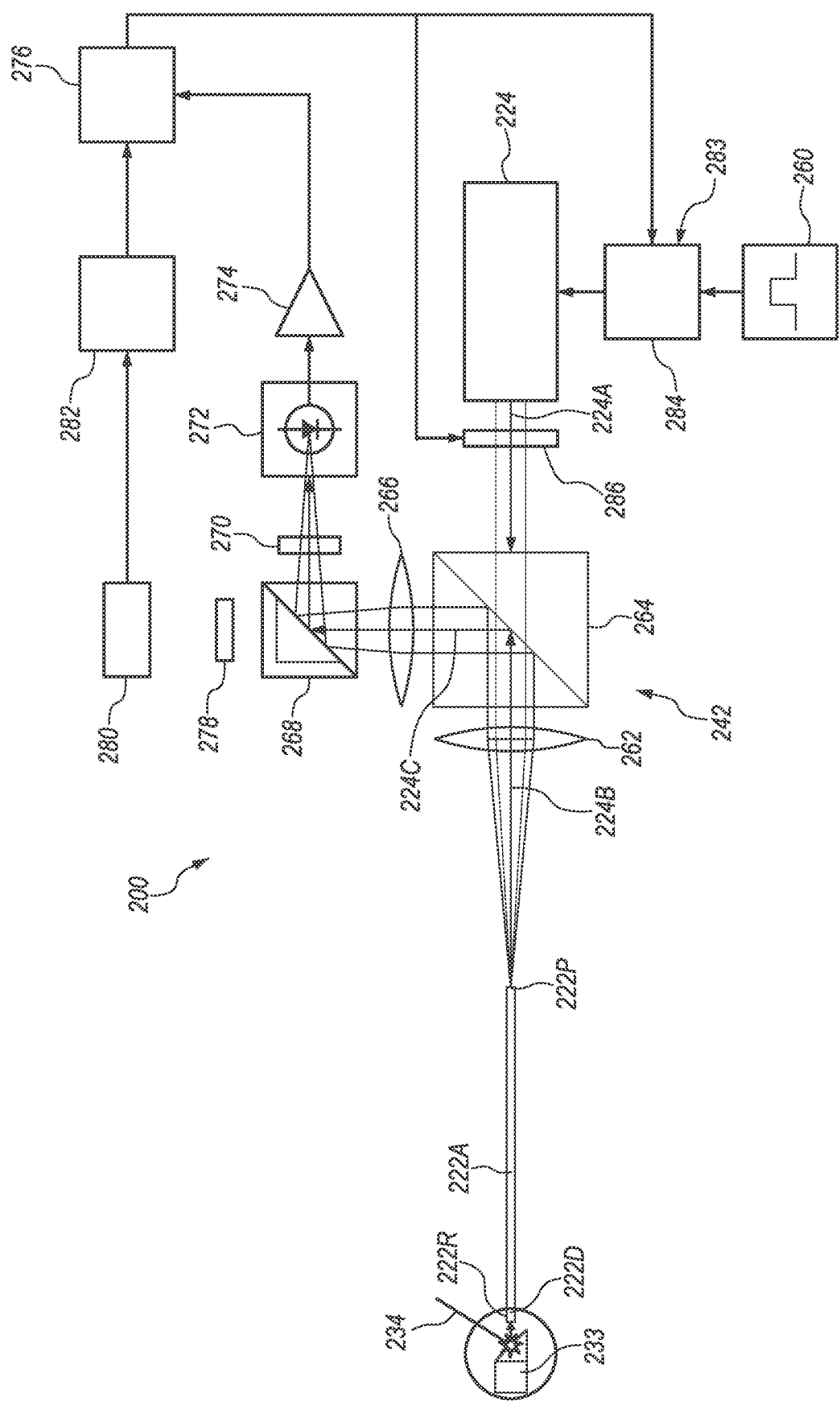
FIG. 2A is a simplified schematic view of a portion of an embodiment of the catheter system including an embodiment of the optical analyzer assembly, the optical analyzer assembly being utilized in a first application.
Figure 2B:
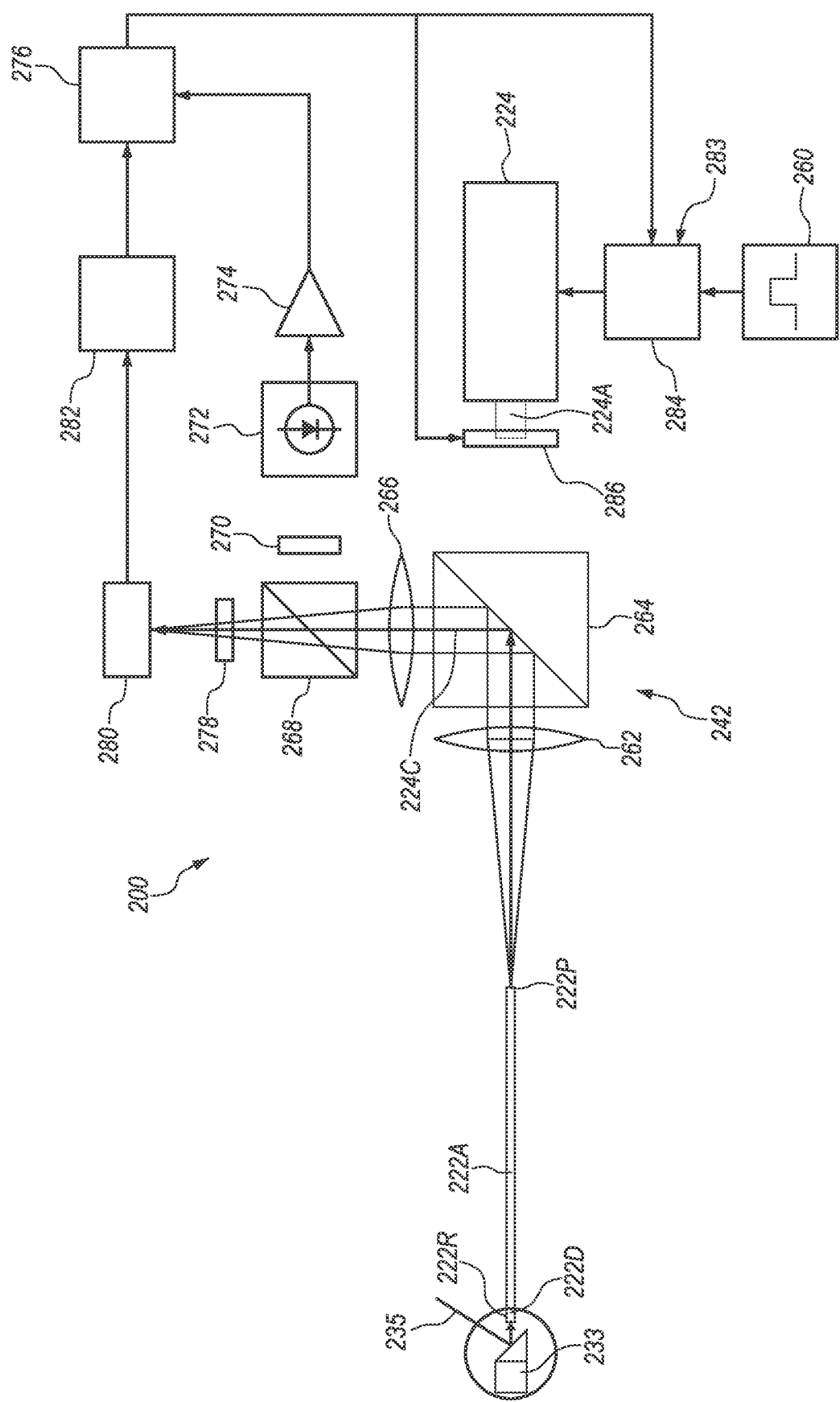
FIG. 2B is a simplified schematic view of a portion of the catheter system including the optical analyzer assembly of FIG. 2A, the optical analyzer assembly being utilized in a second application.

FIG. 2A is a simplified schematic view of a portion of an embodiment of the catheter system 200 including an embodiment of the optical analyzer assembly 242. As shown in FIG. 2A, the optical analyzer assembly 242 is being utilized in a first application. FIG. 2B is a simplified schematic view of a portion of the catheter system 200 including the optical analyzer assembly 242 of FIG. 2A. As shown in FIG. 2B, the optical analyzer assembly 242 is being utilized in a second application.

The design of the catheter system 200 is substantially similar to the embodiments illustrated and described herein above. It is appreciated that various components of the catheter system 200, such as are shown in FIG. 1, are not illustrated in FIGS. 2A and 2B for purposes of clarity and ease of illustration. However, it is appreciated that the catheter system 200 will likely include most, if not all, of such components.

As shown in FIGS. 2A and 2B, the catheter system 200 again includes a light source 224 that is configured to generate first light energy in the form of a source beam 224A, such as a pulsed source beam, that can be selectively and/or alternatively directed to and received by each light guide 222A (only one light guide is illustrated in FIGS. 2A and 2B) as an individual guide beam 224B (illustrated in FIG. 2A). In one non-exclusive embodiment, the light source 224 is an infrared laser source, and the light guide 222A is a small diameter, multimode optical fiber. In the embodiment illustrated in FIGS. 2A and 2B, a pulse generator 260 is coupled to the light source 224. The pulse generator 260 is configured to trigger the light source 224, which, thus, emits an energy pulse as the source beam 224A.

In certain embodiments, as shown in FIG. 2A, the source beam 224A from the light source 224 passes through a first optical element 262, such as a coupling and/or focusing lens, that is configured to focus the source beam 224A as the individual guide beam 224B down onto a guide proximal end 222P of the light guide 222A, thereby coupling the individual guide beam 224B in the form of the pulse of infrared energy (the first light energy) into the light guide 222A. Subsequently, the individual guide beam 224B travels along and/or through the light guide 222A as the first light energy and energizes a plasma generator 233 that is positioned and/or incorporated at or near a guide distal end 222D of the light guide 222A. The plasma generator 233 utilizes the pulse of infrared energy to create a localized plasma 234 (such as in the form of a plasma bubble or plasma flash) in the balloon fluid 132 (illustrated in FIG. 1) within the balloon interior 146 (illustrated in FIG. 1) of the balloon 104 (illustrated in FIG. 1).

As shown in FIG. 2A, upon creation of the plasma 234 in the balloon fluid 132 within the balloon interior 146, in various embodiments, a pulse of broad-spectrum light energy emitted from the plasma flash 234 in the form of second light energy is coupled back into the guide distal end 222D of the light guide 222A via a distal light receiver 222R. Such pulse of broad-spectrum light energy (second light energy) then travels back along and/or through the light guide 222A from where it is emitted from the guide proximal end 222P of the light guide 222A as the second light energy 224C.

Additionally, or in the alternative, as shown in FIG. 2B, in some applications, ambient light 235 near the guide distal end 222D of the light guide 222A can be coupled into the guide distal end 222D of the light guide 222A via the distal light receiver 222R. Such ambient light energy (second light energy) then travels along and through the light guide 222A toward the guide proximal end 222P of the light guide 222A, from where it is emitted as the second light energy 224C (also sometimes referred to as an "ambient energy beam" in this application).

As described in detail herein, the optical analyzer assembly 242 is configured to effectively monitor the performance, reliability, safety and proper usage of the catheter system 200 by optically analyzing the second light energy emitted from the guide proximal end 222P of the light guide 222A. Stated in another manner, the optical analyzer assembly 242 is configured to effectively monitor the performance, reliability, safety and proper usage of the catheter system 200 by optically analyzing (i) the second light energy 224C that is generated as a result of the plasma flash 234 created by the plasma generator 233 in the balloon fluid 132 within the balloon interior 146 of the balloon 104, and/or (ii) the second light energy 224C that is in the form of an ambient energy beam 235 that is coupled into the guide distal end 222D of the light guide 222A via the distal light receiver 222R.

The design of the optical analyzer assembly 242 can be varied to suit the specific requirements of the catheter system 200. In particular, in the embodiment shown in FIGS. 2A and 2B, the optical analyzer assembly 242 includes one or more of a first beamsplitter 264, the first optical element 262, a second optical element 266, such as an imaging lens in one non-exclusive embodiment, a second beamsplitter 268, a first filter 270, a photodetector 272, an amplifier 274, control electronics 276, which can include one or more processors or circuits, a second filter 278, an imaging device 280, such as a camera or other suitable imaging device, a device controller 282, and a safety shutdown system 283. As shown, the safety shutdown system 283 can include one or more of a safety interlock 284 and a shutter 286. Alternatively, in other embodiments, the optical analyzer assembly 242 and/or the safety shutdown system 283 can include more components or fewer components than what is specifically illustrated and described herein. Still alternatively, in still other embodiments, the various components of the optical analyzer assembly 242 can be positioned in a different manner than what is specifically illustrated in FIGS. 2A and 2B.

As illustrated in the first application shown in FIG. 2A, the first beamsplitter 264, such as a dichroic beamsplitter in one embodiment, is positioned in the optical path of the source beam 224A between the light source 224 and the guide proximal end 222P of the light guide 222A. In certain embodiments, the beamsplitter 264 is configured to pass light for wavelengths longer than those visible to the photodetector 272 to provide the individual guide beam 224B that is directed toward the guide proximal end 222P of the light guide 222A. Such threshold wavelength can be referred to as the cutoff wavelength. The beamsplitter 264 is further configured to reflect all light having a wavelength that is shorter than the cutoff wavelength. As illustrated in this embodiment, the first optical element 262 is positioned between the first beamsplitter 264 and the light guide 222A and is configured to focus the individual guide beam 224B down onto the guide proximal end 222P of the light guide 222A, thereby coupling the individual guide beam 224B into the light guide 222A.

The first light energy of the individual guide beam 224B is guided along the light guide 222A from the guide proximal end 222P to the guide distal end 222D and energizes the plasma generator 233 that is positioned and/or incorporated at or near a guide distal end 222D of the light guide 222A. The plasma generator 233 utilizes the pulse of infrared energy to create a localized plasma 234 in the balloon fluid 132 within the balloon interior 146 of the balloon 104. A pulse of broad-spectrum light energy emitted from the plasma flash 234 as the form of the second light energy is then coupled back into the guide distal end 222D of the light guide 222A, and travels back along and/or through the light guide 222A from where it is emitted from the guide proximal end 222P of the light guide 222A as the second light energy 224C.

As illustrated in FIG. 2A, the second light energy 224C emitted from the guide proximal end 222P of the light guide 222A is collimated by the first optical element 262 before being directed back toward the first beamsplitter 264. At least a portion of the second light energy 224C is then redirected and/or reflected by the first beamsplitter 264 toward the second beamsplitter 268. The second optical element 266 is positioned in the optical path of the redirected portion of the second light energy 224C between the first beamsplitter 264 and the second beamsplitter 268. The optics of the second optical element 266 focus the collimated second light energy 224C toward the second beamsplitter 268. The second beamsplitter 268 then redirects and/or reflects a portion of the collimated second light energy 224C through the first filter 270, such as a bandpass filter in certain embodiments, and onto the photodetector 272, thus forming an image of the guide proximal end 222P of the light guide 222A onto the photodetector 272, and thereby coupling the second light energy 224C emitted from the guide proximal end 222P of the light guide 222A onto the photodetector 272. In certain embodiments, the photodetector 272 can be a photodiode or another suitable type of photodetector. With such design, the visible light emitted from the plasma flash 234 formed at the guide distal end 222D of the light guide 222A is collected by the photodetector 272.

In some embodiments, the photodetector 272 generates a signal that is based on the visible light emitted from the plasma formed at the guide distal end 222D of the light guide 222A that has been collected by the photodetector 272. As shown in FIG. 2A, the signal from the photodetector 272 is then directed to the amplifier 274 and the control electronics 276, where detection of and intensity evaluation of the plasma flash 234 are determined. In particular, in certain embodiments, the signal from the photodetector 272 is directed toward the amplifier 274 where the signal from the photodetector 272 is amplified. The amplified signal is thus utilized within the control electronics 276 to determine the intensity of the plasma flash 234 that occurred in the balloon fluid 132 within the balloon interior 146.

In certain embodiments, the pulse from the amplified photodetector signal can be gated using a discriminator (not shown), such as a discriminator circuit, that is triggered by the pulse from the pulse generator 260. This information can then be used within the control electronics 276 to determine when the plasma flash 234 occurred in the balloon fluid 132 within the balloon interior 146. More specifically, the control electronics 276 can compare the timing of the original pulse of energy from the light source 224, as triggered by the pulse generator 260, with the timing of the amplified photodetector signal, as gated using the discriminator, to determine when the plasma flash 234 occurred in the balloon fluid 132 within the balloon interior 146.

In some embodiments, the control electronics 276 can be included as part of the system controller 126 (illustrated in FIG. 1). Alternatively, the control electronics 276 can be provided independently of the system controller 126 and can be in electrical communication with the system controller 126.

It is appreciated that there are numerous other configurations for the photodetector 272 that is needed to detect and analyze the light pulse returning from the light guide 222A in the form of the second light energy 224C. For example, in another embodiment, the photodetector 272 can be a spectrometer that provides intensity and wavelength information about the second light energy 224C. In such embodiment, this information can be used to generate a spectral (or flash) signature to further identify specific conditions or events in the light guide 222A and/or the plasma generator 233. More particularly, the small quantities of material comprising the plasma generator 233 will be vaporized during its regular operation. These will produce a spectral line that would be distinct. It is further appreciated that this approach could also be used to differentiate between a functioning plasma generator 233 and a broken or damaged light guide 222A. This could also be used to monitor for external light entering the light guide 222A and/or the catheter system 200 such as room light spectral signatures.

Another application of the present invention would monitor the condition of the light guides 222A for the plasma generators 233. The light conducted back through the light guides 222A when the light guides 222A are first coupled into the catheter system 200 could be monitored to determine that all light guides 222A are intact.

Thus, as described and illustrated in relation to FIG. 2A, the first application for the present invention involves direct detection of the light pulse created by the plasma flash 234 in the balloon fluid 132 within the balloon interior 146. The optical analyzer assembly 242 can be utilized to indicate the intensity of the light pulse, its spectrum, and when it occurs relative to the input pulse from the light source 224. This can be interpreted as follows:

1) The light pulse must occur after a time interval determined by the length of the light guide 222A and the duration of the input energy pulse from the light source 224. If the detected light pulse has the correct intensity and occurs within a specific time window, it is an indication that the plasma generator 233 functioned correctly.

2) If no light pulse is detected at all, this is an indication of a failure of the plasma generator 233, the light source 224 and/or the catheter system 200 as a whole.

3) If a smaller light pulse is detected that occurs too early relative to the energy pulse from the light source 224, this would be an indication of a failure of and/or damage to the light guide 222A.

4) If the light pulse is detected as having a different spectrum or missing a spectral line or signature, this could be used to indicate a failure of the catheter system 200.

In the event of any detected failures of the plasma generator 233, the light source 224, the light guide 222A and/or the catheter system 200 as a whole, the control electronics 276 can be configured to send a signal to the safety shutdown system 283 to shutdown operation of the catheter system 200. More particularly, in this embodiment, the signal from the control electronics 276 to the safety shutdown system 283 can be used to activate the safety interlock 284, which blocks the signal from the pulse generator 260 to the light source 224, thus effectively stopping any generation of light pulses from the light source 224. Additionally, or in the alternative, the signal from the control electronics 276 to the safety shutdown system 283 can be used to activate the shutter 286 which can be closed, thereby blocking any light pulses from the light source 224 that would otherwise be directed toward and coupled into the light guide 222A. With such safety shutdown system 283, potential harms to the patient 109 or operator can be effectively inhibited.

Referring now to FIG. 2B, the second application for the optical analyzer assembly 242 is illustrated and described. In particular, in this second application, the proper usage of the catheter system 200 can be initially monitored prior to any generation of energy pulses by the light source 224.

As shown, the distal light receiver 222R can be configured to receive any ambient light 235 that may be present in the area of the guide distal end 222D of the light guide 222A. In particular, any visible ambient light 235 present in the area of the guide distal end 222D of the light guide 222A can be coupled into the guide distal end 222D of the light guide 222A via the distal light receiver 222R as second light energy 224C, in the form of an ambient energy beam.

The second light energy 224C travels along and/or through the light guide 222A from the guide distal end 222D to the guide proximal end 222P from where it is emitted from the guide proximal end 222P of the light guide 222A. As illustrated in FIG. 2B, the second light energy 224C emitted from the guide proximal end 222P of the light guide 222A is collimated by the first optical element 262 before being directed toward the first beam splitter 264. At least a portion of the second light energy 224C is then redirected and/or reflected by the first beamsplitter 264 toward the second beamsplitter 268. The second optical element 266 is positioned in the optical path of the redirected portion of the second light energy 224C between the first beamsplitter 264 and the second beamsplitter 268. The optics of the second optical element 266 focus the collimated second light energy 224C toward the second beamsplitter 268. The second beamsplitter 268 then transmits at least a portion of the collimated second light energy 224C through the second filter 278, such as a short pass filter in certain embodiments, and onto the imaging device 280, thus forming an image of the guide proximal end 222P of the light guide 222A onto the imaging device 280, and thereby coupling the second light energy 224C emitted from the guide proximal end 222P of the light guide 222A onto the imaging device 280. Thus, in suitable arrangements, the first optical element 262 and the second optical element 266 can cooperate to create a high-resolution image of the guide proximal end 222P of the light guide 222A onto the imaging device 280. In certain embodiments, the imaging device 280 can be an area sensor such as a CCD or CMOS camera or another suitable type of imaging device. With such design, the visible ambient light 235 collected at the guide distal end 222D of the light guide 222A is collected by the imaging device 280.

In some embodiments, the imaging device 280, under control of the device controller 282, generates a signal that is based on the visible ambient light 235 collected at the guide distal end 222D of the light guide 222A that has been collected by the imaging device 280. As shown in FIG. 2B, the signal from the imaging device 280 is then directed to the control electronics 276, where detection of any potential ambient light 235 near the guide distal end 222D of the light guide 222A is determined. In particular, in certain embodiments, the signal from the imaging device 280 is utilized within the control electronics 276 to determine if any ambient light 235 is present near the guide distal end 222D of the light guide 222A.

If no ambient light 235 is detected by the optical analyzer assembly 242 as having been collected from the area near the guide distal end 222D of the light guide 222A, this is an indication that the catheter system 200 is not being utilized in an improper manner. However, if the optical analyzer assembly 242 detects variation in the light returning from the light guide 222A, thereby signaling ambient light 235 originating from outside the catheter system 200, this is an indication that the catheter system 200 is being used in an unintended condition. In such situation, the control electronics 276 can be configured to send a signal to the safety shutdown system 283 to shutdown operation of the catheter system 200. More particularly, in this embodiment, the signal from the control electronics 276 to the safety shutdown system 283 can be used to activate the safety interlock 284, which blocks any signal from the pulse generator 260 to the light source 224, thus effectively stopping any generation of light pulses from the light source 224. Additionally, or in the alternative, the signal from the control electronics 276 to the safety shutdown system 283 can be used to activate the shutter 286 which can be closed, thereby blocking any light pulses from the light source 224 that would otherwise be directed toward and coupled into the light guide 222A. With such safety shutdown system 283, potential harms to the patient 109 or operator can be effectively inhibited.

As described in relation to FIGS. 2A and 2B, the optical analyzer assembly 242 utilizes the second beamsplitter 268 and separate filters 270, 278 to couple the second light energy 224C to both the imaging device 280 (an area sensor) and the photodetector 272 (a single element photodetector such as a photodiode). However, it is appreciated that the noted applications for the catheter system 200 and/or the optical analyzer assembly 242 can be implemented in any suitable manner, and can be done in a somewhat different manner that what has been described in detail herein. For example, in one non-exclusive alternative embodiment, the photodetector 272 of the optical analyzer assembly 242 can be used to monitor for ambient light 235 coupled into the guide distal end 222D of the light guide 222A, as well as being used to monitor the light pulse created by the plasma flash 234 in the balloon fluid 132 within the balloon interior 146. In such alternative embodiment, the imaging device 280 would not be used or could be omitted from the catheter system.

In summary, the applications of the optical analyzer assembly 242, as illustrated in FIGS. 2A and 2B, which is configured to monitor nominal operation of the catheter system 200 as well as potential misuse of the catheter system 200, can include the general steps of:

(1) The catheter system starts up from a standby mode;

(2) The catheter system continuously monitors usage, via the optical analyzer assembly and/or the imaging device (sometimes referred to as an image sensor subsystem), looking for evidence of ambient light conducted from the guide distal end of the light guide (as evidence of potential improper usage of the system). The optical analyzer assembly and/or the imaging device would monitor the image of the end face of the light guide at a high frame rate looking for non-zero condition or a prescribed variation in signal over time;

(3) A pulse generator sends a trigger to the light source (IR laser) to emit an energy pulse. This could be initiated, for example, by an operator pushing an activation button;

(4A) The image sensor subsystem detects no light returning from the light guide signaling acceptable use parameters;

(4B) The image sensor subsystem detects variation in the light returning from the light guide signaling ambient light originating from outside. This is an indication that the catheter system is being used in an unintended condition and sends a signal to the control electronics;

(5A) If step (4A) is met, the control electronics enable usage of the light source through deactivating the safety interlock and/or opening the shutter that otherwise interrupts the source beam. The process then proceeds to step (6);

(5B) If step (4B) is met, the control electronics lock out the light source through activation of the safety interlock and/or closing the shutter to stop or interrupt the source beam. The process is then stopped and does not proceed and/or moves back to step (1) after the catheter is repositioned as necessary;

(6) The guide beam in the form of first light energy is focused down onto the guide proximal end of the light guide, coupling the pulse of IR energy into it;

(7) The pulse of IR energy in the form of the first light energy travels through the light guide and energizes the plasma generator. The plasma generator creates a localized plasma in the balloon fluid within the balloon interior of the balloon;

(8) The pulse of broad-spectrum light energy emitted from the plasma in the form of second light energy is coupled back into the guide distal end of the light guide via the distal light receiver, and is conducted back through the light guide to the proximal end;

(9) The beamsplitters and optical elements cooperate to form an image of the end face of the light guide on the photodetector;

(10) The signal from the photodetector is amplified. This signal can be used to determine the intensity of the plasma event;

(11) The pulse from the amplified photodetector is conditioned and this information is used to determine when the plasma event occurred;

(12) If no light pulse is detected at all, if a smaller light pulse is detected that occurs too early relative to the energy pulse from the light source, or if the light pulse is detected as having a different spectrum or missing a spectral line or signature, this could be used to indicate a failure of the plasma generator, the light source, the light guide and/or the catheter system as a whole; and

(13) If (12) is met, the control electronics lock out the light source through activation of the safety interlock and/or closing the shutter to stop or interrupt the source beam. The process is then stopped and does not proceed.

Thus, as noted above, the optical analyzer assembly 242 of the present invention addresses multiple potential issues with the performance, reliability, safety and proper usage of an IVL catheter, in particular one that utilizes an energy source, e.g., a light source such as a laser source, to create a localized plasma which in turn induces a high energy bubble in the balloon fluid 132 within the balloon interior 146 of the balloon 104. For example, as noted above, issues that are addressed by the present invention include, but are not limited to: 1) optical detection of when the IVL catheter is in position at a treatment site, 2) optical detection of conditions under which the IVL catheter may be misused, 3) optical detection of successful firing of the energy source, such as the laser source, to generate the plasma within the balloon interior, 4) accurate determination of the energy output of the plasma generator, 5) optical detection of a failure of the catheter system to generate the desired plasma within the balloon interior, and 6) optical detection of a failure of the energy guide at any point along the length of the energy guide.

The remaining Figures are provided to further illustrate and describe certain features and aspects of the present invention in terms of operation of and analysis by the optical analyzer assembly, and subsequent determination of operational conditions within the catheter system.

Figure 3A:
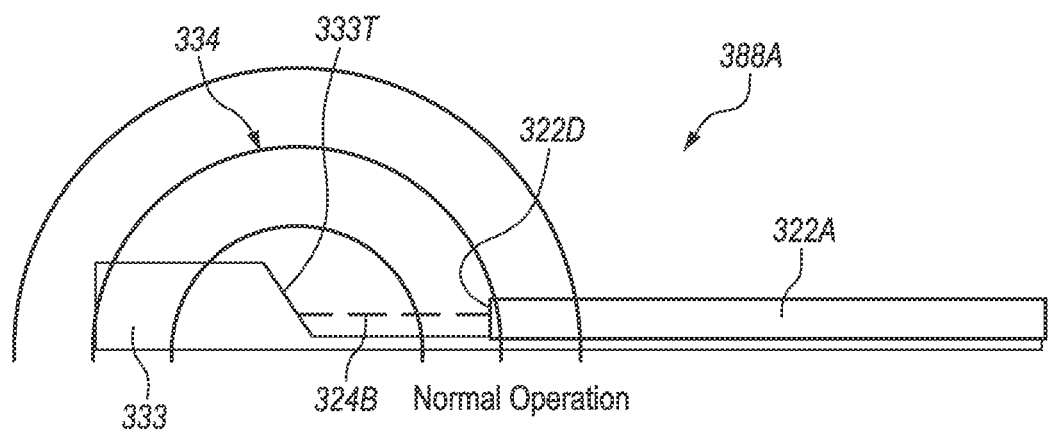
FIGS. 3A-3F are simplified schematic illustrations of operational conditions that may be identified by the optical analyzer assembly during operation of the catheter system of FIG. 1.
Figure 3B:
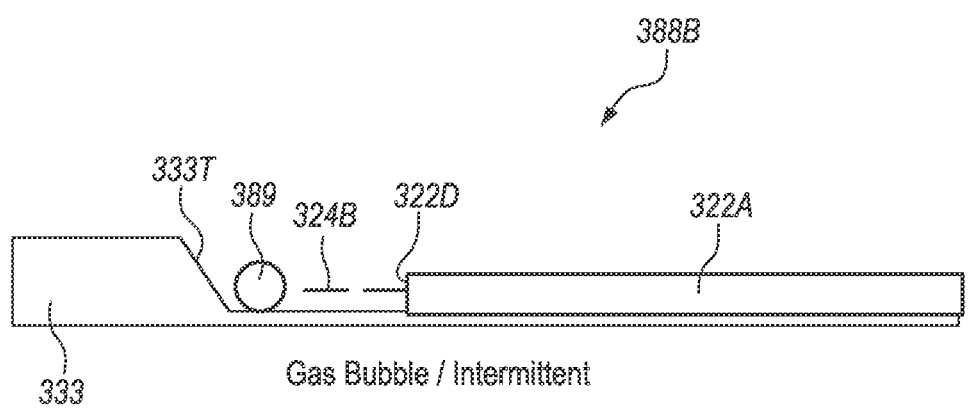
Figure 3C:
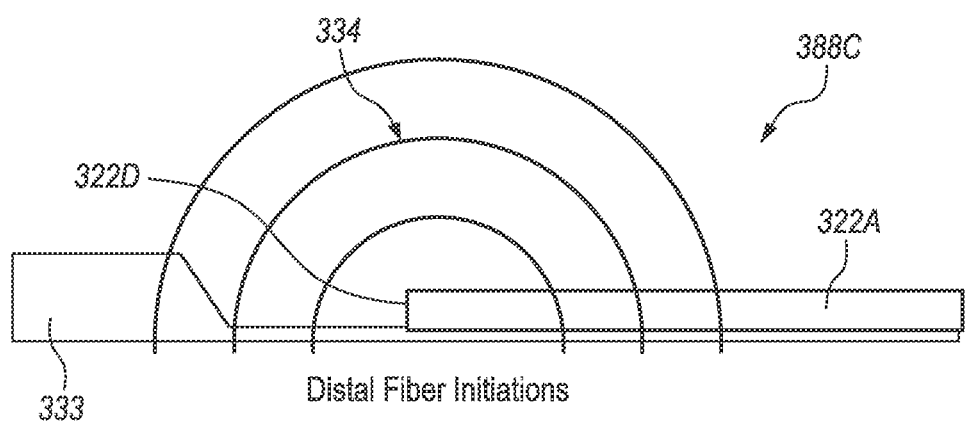
Figure 3D:
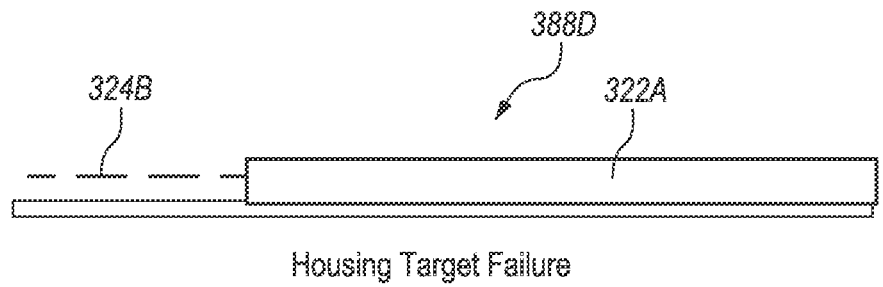
Figure 3E:
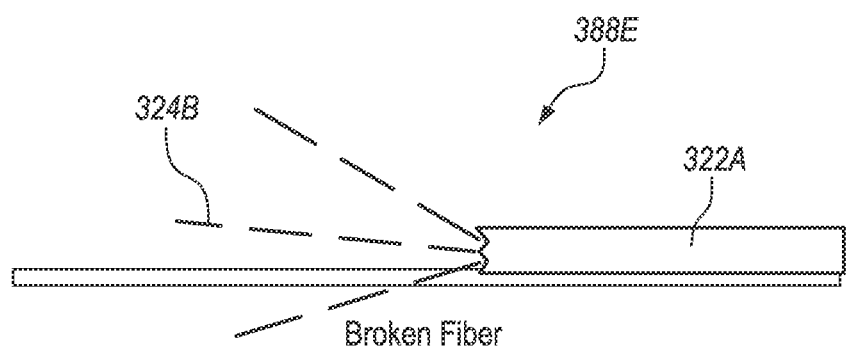
Figure 3F:
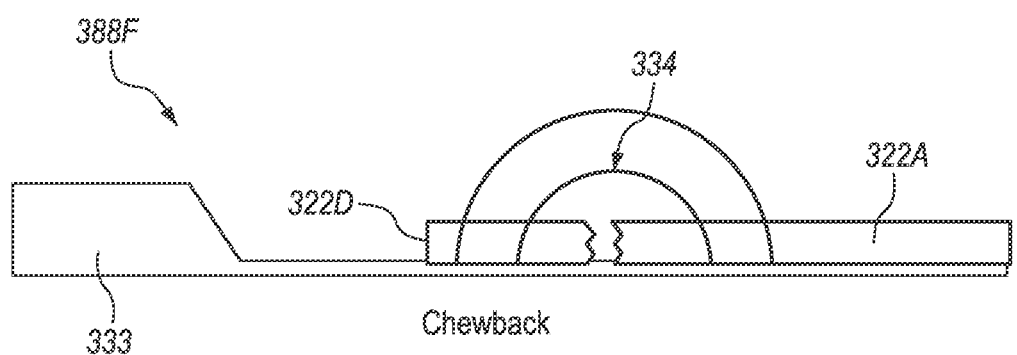

FIGS. 3A-3F are simplified schematic illustrations of operational conditions that may be identified by the optical analyzer assembly during operation of the catheter system of FIG. 1. More specifically, FIG. 3A is a simplified schematic illustration of a first operational condition 388A that may be identified by the optical analyzer assembly during operation of the catheter system; FIG. 3B is a simplified schematic illustration of a second operational condition 388B that may be identified by the optical analyzer assembly during operation of the catheter system; FIG. 3C is a simplified schematic illustration of a third operational condition 388C that may be identified by the optical analyzer assembly during operation of the catheter system; FIG. 3D is a simplified schematic illustration of a fourth operational condition 388D that may be identified by the optical analyzer assembly during operation of the catheter system; FIG. 3E is a simplified schematic illustration of a fifth operational condition 388E that may be identified by the optical analyzer assembly during operation of the catheter system; and FIG. 3F is a simplified schematic illustration of a sixth operational condition 388F that may be identified by the optical analyzer assembly during operation of the catheter system.

As shown in FIG. 3A, the light guide 322A and the plasma generator 333 are illustrated where the first operational condition 388A is a normal operation condition. In such normal operation condition, plasma 334 and a subsequent acoustic wave (illustrated as a series of arced lines) is generated substantially directly adjacent to the plasma generator 333 when the first light energy 324B is directed from the guide distal end 322D of the light guide 322A toward the plasma generator 333 and thus impinges on a target surface 333T of the plasma generator 333.

In FIG. 3B, the light guide 322A and the plasma generator 333 are illustrated in the second operational condition 388B where intermittent gas bubble production conditions exist. In such second operational condition 388B, gas bubbles 389 (one gas bubble 389 is shown in FIG. 3B) formed within the balloon fluid 132 (illustrated in FIG. 1) are found between the guide distal end 322D of the light guide 322A and the plasma generator 333 that optically impact the directing of the first light energy 324B toward the target surface 333T of the plasma generator 333. Thus, little to no plasma (not shown in FIG. 3B) is generated and the resulting flash signature may have a lower pulse maximum value than would be desired in order to most effectively disrupt the vascular lesions 106A (illustrated in FIG. 1) at the treatment site 106 (illustrated in FIG. 1). Under such conditions, the operator may be able to treat the fluid pump 138 (illustrated in FIG. 1) and/or the inflation conduit 140 (illustrated in FIG. 1) in order to inhibit the creation of such intermittent gas bubbles 389 without the need to shut down operation of the catheter system 100 (illustrated in FIG. 1) and replace the light guide 322A and/or the plasma generator 333.

In FIG. 3C, the light guide 322A and the plasma generator 333 are illustrated in the third operational condition 388C where guide distal end plasma initiation conditions exist. In such third operational condition 388C, there may be some debris substantially adjacent to the guide distal end 322D of the light guide 322A which causes plasma 334 and a subsequent acoustic wave (illustrated as a series of arced lines) to be generated at such point substantially adjacent to the guide distal end 322D of the light guide 322A rather than substantially directly adjacent to the plasma generator 333. The resulting flash signature may have a higher pulse maximum value than under nominal conditions. This may also impact the ability of the catheter system 100 (illustrated in FIG. 1) to most effectively disrupt the vascular lesions 106A (illustrated in FIG. 1) at the treatment site 106 (illustrated in FIG. 1). However, the third operational condition 388C may be cleared up with subsequent cleaning of such areas within the balloon 104 (illustrated in FIG. 1) without the need to shut down operation of the catheter system 100 and replace the light guide 322A and/or the plasma generator 333.

In FIG. 3D, the light guide 322A is illustrated in the fourth operational condition 388D where housing/target failure conditions exist. In such fourth operational condition 388D, there is a failure to generate the desired plasma flash in the balloon fluid 132 (illustrated in FIG. 1) within the balloon interior 146 (illustrated in FIG. 1) from the first light energy 324B being directed by the light guide 322A. Under such condition, the resulting flash signature has a lower pulse maximum value. This provides evidence that there is a failure of the light guide 322A and/or the plasma generator 333 (illustrated, for example, in FIG. 3A) during the process of trying to generate the desired plasma flash in order to effectively disrupt the vascular lesions 106A (illustrated in FIG. 1) at the treatment site 106 (illustrated in FIG. 1). Thus, in order to correct or overcome this condition, use of the catheter system 100 (illustrated in FIG. 1) is stopped and the light guide 322A and/or the plasma generator 333 can be removed and replaced or the catheter system 100 can be discarded as a whole. It is noted that the plasma generator 333 is not illustrated in FIG. 3D to more clearly illustrate the failure of the desired plasma generation.

In FIG. 3E, the light guide 322A is illustrated in the fifth operational condition 388E where broken light guide (fiber) conditions exist. In such fifth operational condition 388E, little to no plasma (not shown in FIG. 3E) is generated in the balloon fluid 132 (illustrated in FIG. 1) within the balloon interior 146 (illustrated in FIG. 1), and any minimal plasma that is generated would typically have a lower pulse maximum value due to the first light energy 324B being directed in multiple disparate directions away from the guide distal end 322D of the light guide 322A rather than just directly toward the plasma generator 333 (illustrated, for example, in FIG. 3A). It is appreciated that this failure mode can happen anywhere along the length of the catheter, and not just within the balloon. When such fifth operational condition 388E is determined to exist, operation of the catheter system 100 (illustrated in FIG. 1) should be stopped.

In FIG. 3F, the light guide 322A and the plasma generator 333 are illustrated in the sixth operational condition 388F where chewback conditions exist, such as broken light guides 322A along the length of the light guide 322A and at least somewhat spaced apart from the guide distal end 322D. In such sixth operational condition 388F, plasma 334 (illustrated as a series of arced lines) generation can occur in the balloon fluid 132 (illustrated in FIG. 1) within the balloon interior 146 (illustrated in FIG. 1) substantially adjacent to where a break may exist along the length of the light guide 322A. Under such conditions, the resulting flash signature is typically very jagged, increasing and decreasing in magnitude very quickly over time. When such sixth operational condition 388F is determined to exist, any plasma 334 generated is much less likely to be directed in an appropriate manner so as to effectively disrupt the vascular lesions 106A (illustrated in FIG. 1) at the treatment site 106 (illustrated in FIG. 1). Thus, operation of the catheter system 100 (illustrated in FIG. 1) should be stopped.

Figure 4A:
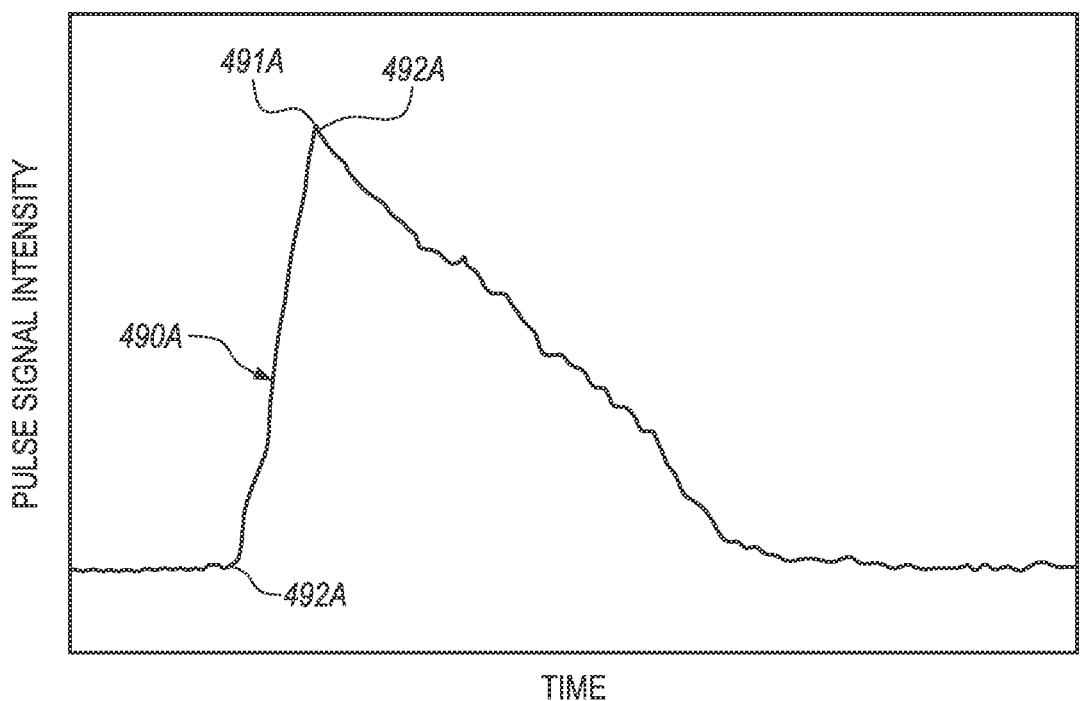
FIG. 4A is a simplified graphical illustration of a representative example of one flash signature that may be identified by the optical analyzer assembly during operation of the catheter system of FIG. 1.
Figure 4B:
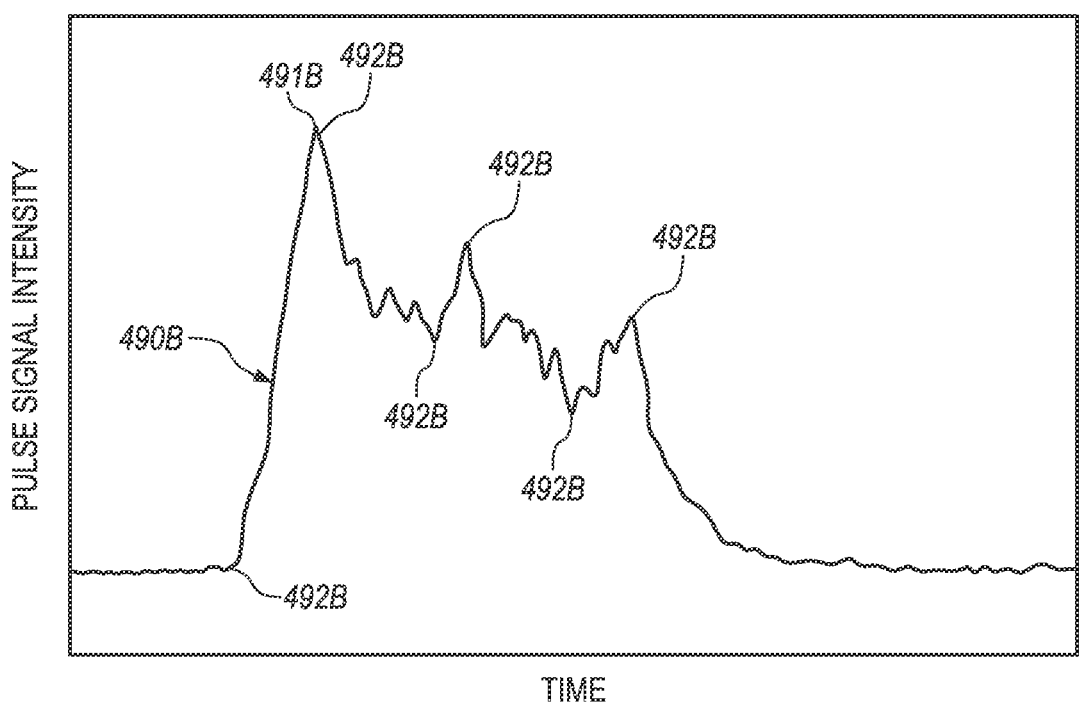
FIG. 4B is a simplified graphical illustration of a representative example of a second, different flash signature that may be identified by the optical analyzer assembly during operation of the catheter system of FIG. 1.

As provided herein, much of the analysis undertaken through use of the optical analyzer assembly involves the capturing of an image of a flash signal (or flash signature) that stems from plasma generation in the balloon fluid within the balloon interior, and the subsequent analysis of the flash signal (or flash signature) as a means to determine the operational condition of the catheter system. It is appreciated that the flash signal (or flash signature) can take any specific form and there are infinite possibilities for all the details incorporated within the flash signal (or flash signature). FIGS. 4A and 4B provide simplified graphical illustrations of just two potential examples of what the flash signal (or flash signature) may look like as captured through use of the optical analyzer assembly.

FIG. 4A is a simplified graphical illustration of a representative example of a first flash signature 490A that may be identified by the optical analyzer assembly 242 (illustrated, for example, in FIG. 2A) during operation of the catheter system 100 of FIG. 1, in terms of flash intensity (Y-axis) versus time (X-axis). More particularly, the first flash signature 490A would be identified by the optical analyzer assembly 242 during the generation of a plasma flash 334 (illustrated in FIG. 3A) from a single pulse of first light energy 324B (illustrated in FIG. 3A) from the light source 124 (illustrated in FIG. 1) through the light guide 322A (illustrated in FIG. 3A). As illustrated, the first flash signature 490A has a single peak 491A and two transitions 492A. In analyzing the peaks in any given flash signature, the largest or highest peak can also be referred to as the "pulse maximum intensity" value or simply the "pulse maximum". In FIG. 4A, the first flash signature 490A only has the single peak 491A, so that single peak 491A would also be referred to as the pulse maximum intensity value, or the "pulse maximum".

FIG. 4B is a simplified graphical illustration of a representative example of a second flash signature 490B that may be identified by the optical analyzer assembly 242 (illustrated, for example, in FIG. 2A) during operation of the catheter system 100 of FIG. 1, in terms of flash intensity (Y-axis) versus time (X-axis). More particularly, the second flash signature 490B would be identified by the optical analyzer assembly 242 during the generation of a plasma flash 334 (illustrated in FIG. 3A) from a single pulse of first light energy 324B (illustrated in FIG. 3A) from the light source 124 (illustrated in FIG. 1) through the light guide 322A (illustrated in FIG. 3A). As illustrated, the second flash signature 490B has three peaks 491B and six transitions 492B. Again, in analyzing the peaks in any given flash signature, the highest peak can also be referred to as the "pulse maximum intensity" value or simply the "pulse maximum". In FIG. 4B, the second flash signature 490B has three peaks 491B, with the first peak 491B being the largest or highest, and thus would also be referred to as the pulse maximum intensity value, or the "pulse maximum".

As referred to herein, a "transition" is defined generally as a change in direction of the slope of the flash signature as shown in the graphical illustration. As shown in FIGS. 4A and 4B, both signals have a transition as the signal quickly climbs from the X-axis. Both signals also have another transition as the signal drops down from the pulse maximum. FIG. 4B has more transitions or volatility in the signal after this point. The exact number of transitions measured in each signal is dependent on the tuning of various parameters. One parameter defines the slope change magnitude required to classify something as a transition and the other is a hysteresis parameter to avoid counting transitions on noise in the signature.

Figure 5:
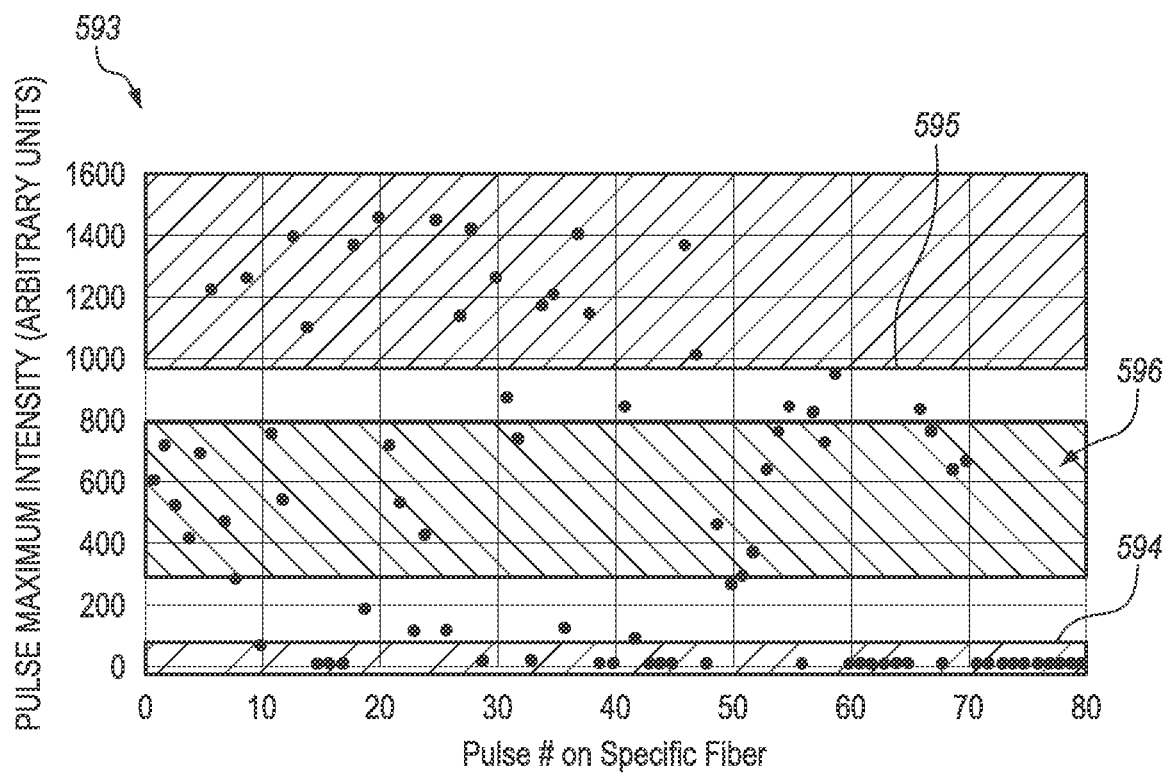
FIG. 5 is a simplified graphical illustration of an example of pulse maximum readings that may be identified by the optical analyzer assembly as pulses of first light energy are sent through a light guide used within the catheter system of FIG. 1.

FIG. 5 is a simplified graphical illustration 593 of an example of pulse maximum intensity readings that may be identified by the optical analyzer assembly from the plasma flashes generated as pulses of first light energy are sent through a light guide used within the catheter system of FIG. 1. As shown, the pulse maximum intensity reading (in arbitrary units) from the plasma flashes generated for each pulse of first light energy being guided through the light guide is shown along the Y-axis, and the pulse number for the specific light guide is shown along the X-axis. Stated in another manner, the Y-axis relates to the maximum value that is found in the flash signature (or flash signal) that is detected by the optical analyzer assembly for any given pulse of first light energy that is sent through the given light guide.

FIG. 5 illustrates both a minimum pulse maximum intensity threshold 594 and a maximum pulse maximum intensity threshold 595 that can be used by the system controller to help define the operational condition of the light guide and/or the plasma generator.

The minimum pulse maximum intensity threshold 594 can be used by the system controller to determine if the operational condition of the light guide is one of intermittent gas bubble production conditions; housing/target failure conditions; and/or broken light guide (fiber) conditions. In any of such operational conditions, the pulse maximum intensity will have a low value that provides an indication that the plasma flash, if any, may not be sufficient to effectively disrupt the vascular lesions at the treatment site.

It is appreciated that a pulse maximum intensity value of at or very near zero would be an indication of any of the conditions described in the previous paragraph, where little or no plasma flash has occurred. Because of this ambiguity in the potential failure mode, the history of all pulses on each fiber can be tracked to distinguish among such conditions, instead of responding to a single instance of no signal detection conditions. As discussed further below, the pulse maximum intensity value would not necessarily have to be zero to indicate such failure conditions because it is always possible that at least some extraneous light may be captured by the distal light receiver and sent back as second light energy from the guide distal end toward the guide proximal end.

In one non-exclusive embodiment, the minimum pulse maximum intensity threshold 594 can be approximately 100 units, such that any registered pulse maximum intensity value at or below 100 units can indicate such undesired operational conditions for the light guide. Alternatively, in other embodiments, the minimum pulse maximum intensity threshold 594 can be approximately 50 units, 75 units, 125 units, 150 units, 175 units, 200 units, or another suitable minimum pulse maximum intensity threshold value.

As further described below in relation to FIG. 7, it is appreciated that to avoid any potential false positive readings for no signal detection conditions, it may be desired to require a certain number of pulses of first light energy to have a pulse maximum intensity value below a no signal detection pulse maximum intensity threshold value, such as 50 units in one non-exclusive embodiment, within a certain range or number of pulses of first light energy, in order for a true positive identification of such no signal detection conditions.

The maximum pulse maximum intensity threshold 595 can be used by the system controller to determine if the operational condition of the light guide is guide distal end plasma initiation conditions. Under such conditions, the pulse maximum intensity of the plasma flash as the second light energy is sent back through the light guide to be optically analyzed by optical analyzer assembly may be higher than under normal operating conditions because the plasma flash is often larger and occurs substantially directly adjacent to the guide distal end of the light guide. Simply stated, under such conditions, more second light energy would be received by the distal light receiver and thus sent back through the light guide in the second direction because such light energy is generated and/or reflected substantially directly adjacent to the guide distal end and thus the distal light receiver.

In one non-exclusive embodiment, the maximum pulse maximum intensity threshold 595 can be approximately 1000 units, such that any registered pulse maximum intensity value at or above 1000 units can indicate such an undesired operational condition for the light guide. Alternatively, in other embodiments, the maximum pulse maximum intensity threshold 595 can be approximately 900 units, 925 units, 950 units, 975 units, 1025 units, 1050 units, 1075 units, 1100 units, 1125 units, 1150 units, or another suitable maximum pulse maximum intensity threshold value.

FIG. 5 further illustrates typical pulse maximum intensity values for the plasma flash when the light guide is operating under normal operating conditions, i.e. a normal pulse maximum intensity range 596. In one non-exclusive embodiment, normal operating conditions can be determined if the normal pulse maximum intensity range 596 is between approximately 300 units and 800 units. Alternatively, the normal pulse maximum intensity range 596 for an indication of normal operating conditions can vary from the noted range, so long as such normal pulse maximum intensity range 596 does not overlap or go beyond the minimum pulse maximum intensity threshold 594 (i.e. below such minimum pulse maximum intensity threshold 594) or beyond the maximum pulse maximum intensity threshold 595 (i.e. above such maximum pulse maximum intensity threshold 595). For example, in certain non-exclusive alternative embodiments, the normal pulse maximum intensity range 596 for the plasma flash can be between approximately 200 units and 900 units; between approximately 250 units and 850 units, between approximately 350 units and 900 units, between approximately 300 units and 850 units, or some other range of suitable pulse maximum intensity values.

Figure 6:
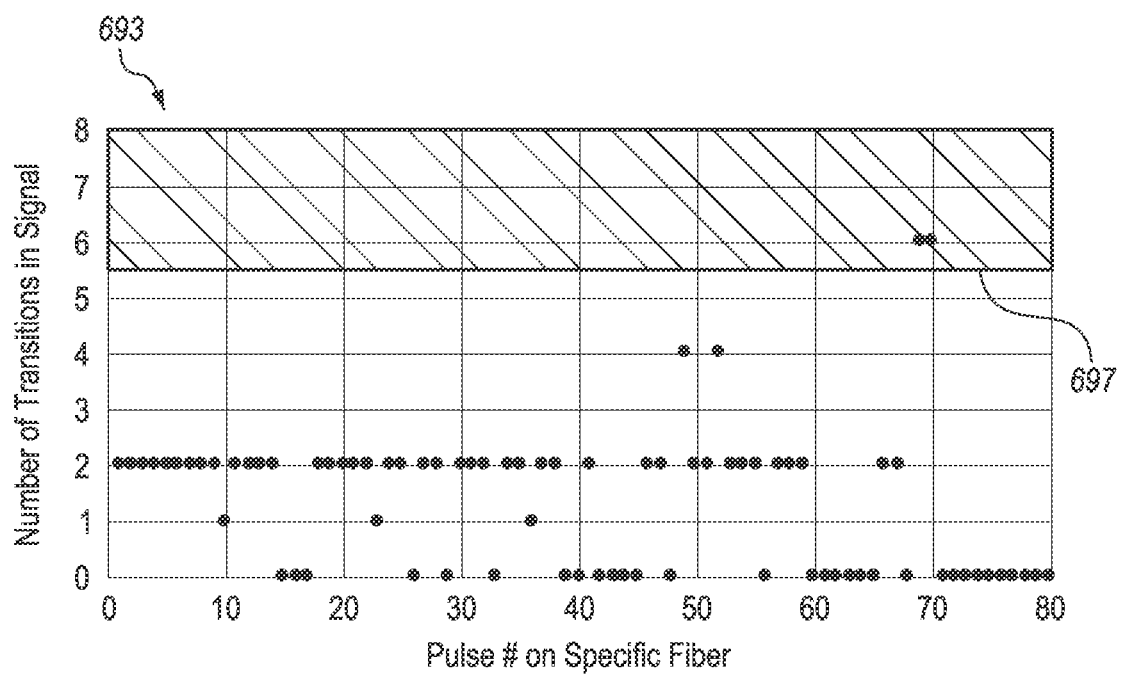
FIG. 6 is a simplified graphical illustration of an example of a number of transitions that may be identified by the optical analyzer assembly within a flash signal generated as pulses of first light energy are sent through a light guide used within the catheter system of FIG. 1.

FIG. 6 is a simplified graphical illustration 693 of an example of a number of transitions that may be identified by the optical analyzer assembly within a flash signal generated as pulses of first light energy are sent through a light guide used within the catheter system of FIG. 1. As shown, the number of transitions identified in the flash signature (or flash signal) for the light guide for any given pulse of first light energy is shown along the Y-axis, and the pulse number for the specific light guide is shown along the X-axis. FIG. 6 provides an indication that the light guide may be suffering from chewback when the number of transitions within the plasma signature for any given pulse of first light energy is above a certain transition threshold 697. In one embodiment, as shown, the transition threshold 697 for identifying the light guide as suffering from chewback can be six transitions. Alternatively, in other embodiments, the transition threshold 697 for identifying the light guide as suffering from chewback can be four transitions, five transitions, seven transitions, eight transitions, nine transitions, ten transitions, or another suitable number of transitions.

It is appreciated that to avoid any potential false positive readings for identifying chewback conditions, it may be desired to require a certain number of pulses of first light energy to have the number of transitions be at or above the transition threshold 697 in order for a true positive identification of chewback conditions. For example, in one non-exclusive embodiment, it may be required to find at least three pulses of first light energy where the number of transitions is at or above the transition threshold to positively identify chewback conditions. Alternatively, in other embodiments, it may be required to find only one or at least two, four, five, six, or some other suitable number of pulses of first light energy where the number of transitions is at or above the transition threshold to positively identify chewback conditions.

Figure 7:
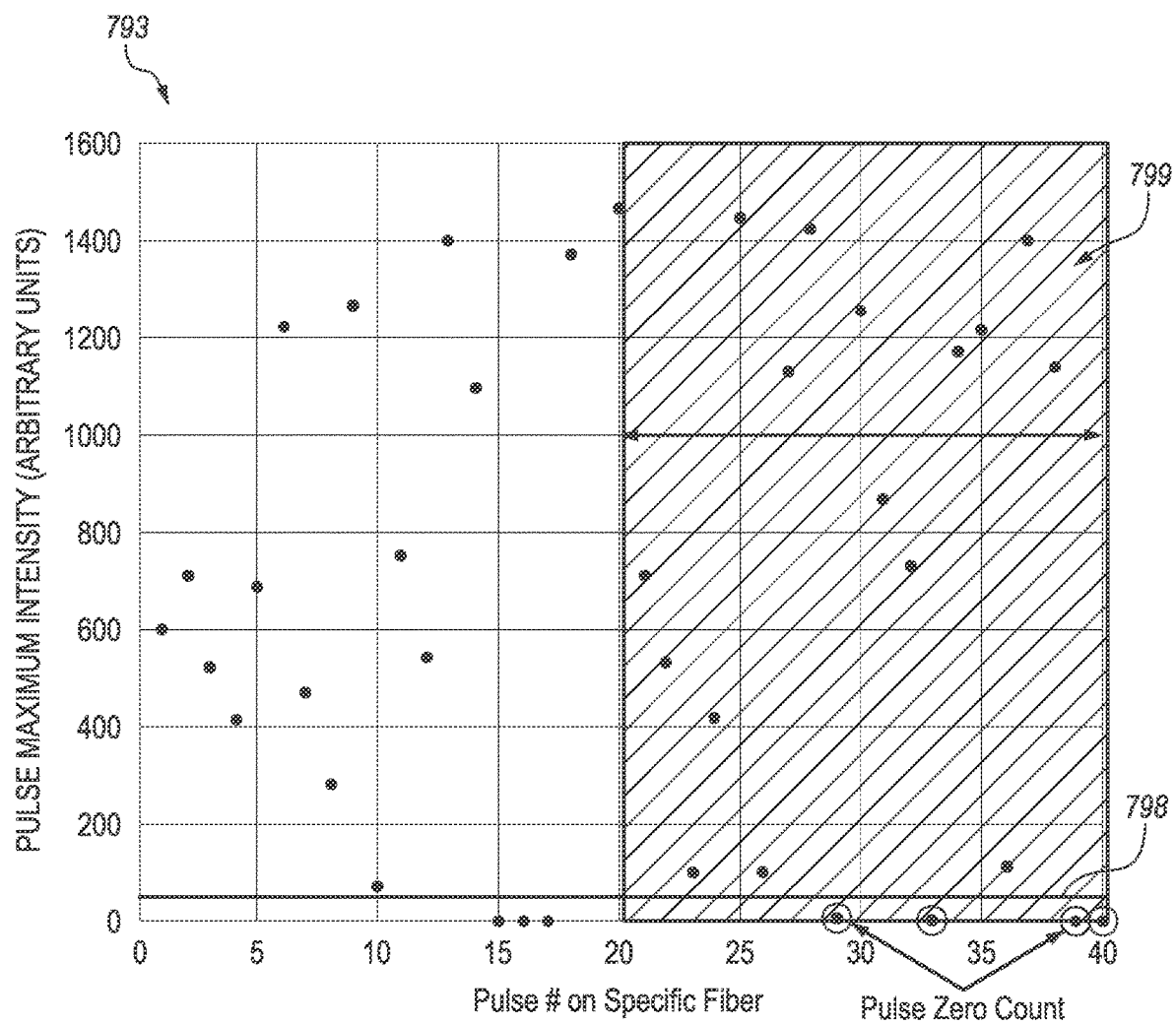
FIG. 7 is a simplified graphical illustration of an example of how no signal detection conditions can be identified by the optical analyzer assembly as pulses of first light energy are sent through a light guide used within the catheter system of FIG. 1.

FIG. 7 is a simplified graphical illustration 793 of an example of how no signal detection conditions can be identified by the optical analyzer assembly as pulses of first light energy are sent through a light guide used within the catheter system of FIG. 1. Similar to FIG. 5, the pulse maximum intensity reading (in arbitrary units) from the plasma flashes generates for each pulse of first light energy being guided through the light guide is shown along the Y-axis, and the pulse number for the specific light guide is shown along the X-axis. Stated in another manner, the Y-axis relates to the highest peak that is found in the flash signature (or flash signal) that is detected by the optical analyzer assembly for any given pulse of first light energy that is sent through the given light guide.

As illustrated, FIG. 7 shows a zero threshold 798 (or no signal detection threshold), and a window zero count 799 (or a no signal detection range). For purposes of effectively establishing a condition of no signal detection (and/or to avoid improperly identifying such a condition), in various embodiments, it may be required to find a certain number of pulses (or zero pulse count) within the window zero count 799 (a given number or range of preceding pulses) that have a pulse maximum intensity value below the zero threshold 798. Stated in another manner, if the number of pulses within the previous window zero count 799 of pulses of first light energy through a given light guide that have a pulse maximum intensity value of less than the zero threshold 798 meets or exceeds the zero pulse count, then the system effectively identifies a no signal detection condition.

It is appreciated that all of the zero threshold 798, the window zero count 799, and the zero pulse count can be varied in the process of endeavoring to positively identify the no signal detection condition. For example, in one non-exclusive embodiment, the zero threshold 798 can be established where the pulse maximum intensity value for a given pulse of first light energy through the light guide is not greater than 50 units. Alternatively, in other embodiments, the zero threshold 798 can be established where the pulse maximum intensity value is no greater than 10 units, 15 units, 20 units, 25 units, 30 units, 35 units, 40 units, 45 units, 55 units, 60 units, 65 units, 70 units, 75 units, or some other suitable number of units.

In one non-exclusive embodiment, the window zero count 799 can refer to a range of 20 pulses over which the defined zero pulse count of pulses of first light energy being sent through the given light guide must have a reading at or below the zero threshold 798 to effectively identify a no signal detection condition. Alternatively, in other embodiments, the window zero count 799 can refer to a range of 15 pulses, 16 pulses, 17 pulses, 18 pulses, 19 pulses, 21 pulses, 22 pulses, 23 pulses, 24 pulses, 25 pulses, 26 pulses, 27 pulses, 28 pulses, 29 pulses, 30 pulses, 31 pulses, 32 pulses, 33 pulses, 34 pulses, 35 pulses, 36 pulses, 37 pulses, 38 pulses, 39 pulses, 40 pulses, or another suitable number of pulses over which the defined zero pulse count of pulses of first light energy being sent through the given light guide must have a reading at or below the zero threshold 798 to effectively identify a no signal detection condition. As utilized herein, the window zero count 799 is specifically the number of previous pulses to look at on a given light guide when determining the no signal detection condition instead of considering the entire history of the light guide.

In one non-exclusive embodiment, the defined zero pulse count can be 11 pulses of first light energy being sent through the given light guide that have a reading at or below the zero threshold 798 within the window zero count 799 range to effectively identify a no signal detection condition. Alternatively, the defined zero pulse count can be 5, 6, 7, 8, 9, 10, 12, 13, 14, 15, 16, 17, 18, 19, 20, or some other suitable number of pulses of first light energy being sent through the given light guide that have a reading at or below the zero threshold 798 within the window zero count 799 range to effectively identify a no signal detection condition.

In one specific, non-exclusive embodiment, if the zero threshold is 50 units, the window zero count is 20 pulses, and the defined zero pulse count is 11 pulses; then to effectively determine a no signal detection condition, one must find at least 11 pulses of first light energy through the given light guide within the preceding 20 pulses which have a pulse maximum intensity value of less than the zero threshold of 50 units.

It is appreciated that the present invention could be used to monitor the location and condition of any device using an optical light source and light guide for energy transmission. One alternative example is nephrolithotomy using laser lithotripsy. In particular, the beamsplitter and optics comprising this invention could be incorporated into a lithotripsy laser system. This would allow continuous monitoring of light in the form of second light energy returning from the guide distal end of the lithotripsy light guide. When the light guide is inserted through the nephroscope into the kidney, the ambient lighting conditions are controlled by the nephroscope illumination. The characteristic and spectrum of the light detected could be used to determine if the light guide is positioned correctly inside the kidney and it is safe to fire the light source. One means of accomplishing this would be using a signal source with specific wavelength characteristics in the scope illumination. For example, an included narrow band source with high intensity that would not be present in external ambient lighting. This could be detected using a bandpass filter ahead of the photodetector. The light source would be locked out until that optical signal was detected, preventing firing the light source and emitting hazardous laser radiation outside of the patient.

In summary, the catheter systems and related methods disclosed herein are configured to monitor the safety, performance, reliability and proper usage of an intravascular lithotripsy (IVL) catheter. In various embodiments, the catheter systems of the present invention utilize an energy source, e.g., a light source such as a laser source or another suitable energy source, which provides energy that is guided by an energy guide, such as a light guide, to create a localized plasma in a balloon fluid within a balloon interior of an inflatable balloon of the catheter. As such, the energy guide can sometimes be referred to as, or can be said to incorporate a "plasma generator" at or near a guide distal end of the energy guide that is positioned within the balloon interior. This localized plasma generates pressure waves that impart pressure onto and induce fractures at a treatment site within or adjacent to a blood vessel or a heart valve within a body of a patient. As used herein, the treatment site can include a vascular lesion such as a calcified vascular lesion or a fibrous vascular lesion, typically found in a blood vessel and/or a heart valve.

In particular, in various embodiments, the catheter systems can include a catheter configured to advance to the treatment site within or adjacent a blood vessel or heart valve within the body of the patient. The catheter includes a catheter shaft, and a balloon that is coupled and/or secured to the catheter shaft. The balloon can include a balloon wall that defines the balloon interior and can be configured to receive the balloon fluid within the balloon interior to expand from a deflated state suitable for advancing the catheter through a patient's vasculature, to an inflated state suitable for anchoring the catheter in position relative to the treatment site. The catheter systems also include one or more energy guides disposed along the catheter shaft and within the balloon. Each energy guide can be configured for generating pressure waves within the balloon for disrupting the vascular lesions.

The catheter systems utilize energy from an energy source, such as first light energy from a light source, to generate the plasma, such as via the plasma generator, within the balloon fluid at or near a guide distal end of the energy guide disposed in the balloon located at the treatment site. The plasma formation can initiate one or more pressure waves and can initiate the rapid formation of one or more bubbles that can rapidly expand to a maximum size and then dissipate through a cavitation event that can launch pressure waves upon collapse. The rapid expansion of the plasma-induced bubbles can generate one or more pressure waves within the balloon fluid retained within the balloon and thereby impart pressure waves upon the treatment site. In some embodiments, the energy source can be configured to provide sub-millisecond pulses of energy from the energy source to initiate plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the treatment site.

As described in detail herein, the catheter systems of the present invention include an optical analyzer assembly that is configured to provide real-time continuous monitoring of the energy emitted from the guide distal end of the energy guide into the balloon interior, which can be used to detect that a plasma event has occurred and to monitor for nominal operation of the catheter system. The optical analyzer assembly is further configured to monitor ambient energy received into the guide distal end of the energy guide, which can be used as a monitor for proper usage and positioning of the catheter system. For example, monitoring of the ambient energy conducted from the distal end of the energy guide starting at the plasma generator can be used to detect the state and condition of the overall device as a monitor for nominal and safe operation. Similarly, measuring variations in the intensity of the conducted energy over a time interval provides an indication of the location of the distal end and plasma generator itself. When located inside of a human body, the ambient energy conducted through the energy guide will be minimal. It would be expected this would be zero, and any baseline minimally variable. Conversely, the energy conducted when the device is located outside the human body will be nonzero and highly variable. This information can be used to determine the location of the distal end of the energy guide. This in turn could be used to assess the condition of the energy guide and determine if the device is performing nominally.

The optical analyzer assembly can also be utilized to measure the intensity of the energy emitted from the energy guide in order to provide an accurate measurement of the energy output of the plasma generator that is incorporated as part of and/or used in conjunction with the energy guide. More specifically, the measurement of the energy output of the plasma generator can be used in conjunction with the known energy input from the energy source to determine the conversion efficiency. Such metric can also be used to assess the condition of the plasma generator and energy guide and determine if the catheter system is performing normally, as well as the number of operation cycles remaining.

In particular, in various embodiments, the present invention comprises a means of sampling second light energy returned from the plasma generator and/or from the balloon interior back through the energy guide. It is appreciated that energy can travel in both, opposing directions along the length of the energy guide. Thus, it is possible to detect energy originating at the guide distal end of the energy guide, or at any other position along the length of the energy guide, at a guide proximal end of the energy guide. Such second light energy that is transmitted back through the energy guide will thus be separated and detected and/or analyzed via the optical analyzer assembly to effectively monitor the safety, performance, reliability and proper usage of the catheter system.

It is appreciated that the continuous monitoring of the energy emitted from the plasma generator, and the measuring of the intensity of the emitted energy, through use of the present invention, addresses multiple potential issues with the safety, performance, reliability and proper usage of an IVL catheter, in particular one that utilizes an energy source to create a localized plasma which in turn produces a high energy bubble inside a balloon catheter. Specific issues this invention addresses include: 1) optical detection of when the IVL catheter is in position at a treatment site, 2) optical detection of conditions under which the IVL catheter may be misused, 3) optical detection of successful firing of the energy source, such as the laser source, to generate the plasma within the balloon interior, 4) accurate determination of the energy output of the plasma generator, 5) optical detection of a failure of the catheter system to generate the desired plasma within the balloon interior, and 6) optical detection of a failure of the energy guide at any point along the length of the energy guide.

It is further appreciated that when improper usage or failure of the catheter system is detected and/or if a failure of the energy guide is detected at any point along the length of the energy guide, the optical analyzer assembly can be configured to automatically stop operation of the catheter system. Thus, in various embodiments, the catheter system and/or the optical analyzer assembly can incorporate and/or include a safety shutdown system that can be selectively activated when warranted to automatically stop operation of the catheter system. In some such embodiments, the safety shutdown system can include one or more of a safety interlock, a shutter and/or other suitable safety shutdown mechanisms that can be incorporated into the optical analyzer assembly. With such design, the optical analyzer assembly is uniquely configured to inhibit dangerous conditions for the patient and the operator of the catheter system.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or a heart valve, the catheter system comprising:
    a light source that generates first light energy;
    a balloon that is positionable substantially adjacent to the treatment site, the balloon having a balloon wall that defines a balloon interior, the balloon interior receiving a balloon fluid;
    a light guide that is configured to receive the first light energy at a guide proximal end and guide the first light energy in a first direction from the guide proximal end toward a guide distal end that is positioned within the balloon interior, the first light energy inducing generation of a plasma within the balloon interior; and
    an optical analyzer assembly that is configured to optically analyze a second light energy from the light guide that moves in a second direction that is opposite the first direction, the optical analyzer assembly including a safety shutdown system that is selectively activated to inhibit the first light energy from the light source from being received by the guide proximal end of the light guide.

2. The catheter system of claim 1 further comprising a pulse generator that is coupled to the light source, the pulse generator being configured to trigger the light source to generate a source beam that is directed toward the light guide.

3. The catheter system of claim 2 wherein the safety shutdown system includes a safety interlock that is selectively activated to block the pulse generator from triggering the generation of the source beam with the light source.

4. The catheter system of claim 2 wherein the safety shutdown system includes a shutter that is selectively activated to block the source beam from being directed toward the light guide.

5. The catheter system of claim 1 wherein the guide distal end includes a distal light receiver that receives the second light energy from within the balloon interior, the second light energy moving through the light guide in the second direction.

6. The catheter system of claim 5 wherein the second light energy that is received by the distal light receiver is emitted from the plasma that is generated in the balloon fluid within the balloon interior.

7. The catheter system of claim 5 wherein the second light energy that is received by the distal light receiver is optically analyzed by the optical analyzer assembly.

8. The catheter system of claim 7 wherein the optical analyzer assembly is configured to optically determine whether or not plasma generation has occurred within the balloon interior.

9. The catheter system of claim 7 wherein the optical analyzer assembly is configured to optically detect a failure of the light guide between the guide proximal end and the guide distal end.

10. The catheter system of claim 7 wherein the optical analyzer assembly is configured to optically detect potential damage to the light guide between the guide proximal end and the guide distal end.

11. The catheter system of claim 1 wherein the optical analyzer assembly includes a beamsplitter and a photodetector, the beamsplitter being configured to receive the second light energy and direct a portion of the second light energy to the photodetector.

12. The catheter system of claim 11 wherein the optical analyzer assembly further includes an optical element that is positioned along a beam path between the beamsplitter and the photodetector, the optical element being configured to couple the portion of the second light energy to the photodetector.

13. The catheter system of claim 11 wherein the photodetector generates a signal based at least in part on visible light that is included with the portion of the second light energy.

14. The catheter system of claim 13 wherein the signal from the photodetector is amplified with an amplifier to provide an amplified signal that is directed to control electronics to determine an intensity of the plasma generation within the balloon interior.

15. The catheter system of claim 1 wherein the optical analyzer assembly includes a beamsplitter and an imaging device, the beamsplitter being configured to receive the second light energy and direct at least a portion of the second light energy to the imaging device.

16. The catheter system of claim 1 wherein the light source includes a laser.

17. The catheter system of claim 1 wherein the light source includes an infrared laser that emits the first light energy in the form of pulses of infrared light.

18. The catheter system of claim 1 wherein the light guide includes an optical fiber.

19. A catheter system for treating a treatment site within or adjacent to a vessel wall or a heart valve, the catheter system comprising:
- a light source that generates first light energy;
- a balloon that is positionable substantially adjacent to the treatment site, the balloon having a balloon wall that defines a balloon interior, the balloon interior receiving a balloon fluid;
- a light guide that is configured to receive the first light energy at a guide proximal end and guide the first light energy in a first direction from the guide proximal end toward a guide distal end that is positioned within the balloon interior; and
- an optical analyzer assembly that is configured to optically analyze a second light energy from the light guide that moves in a second direction that is opposite the first direction, the optical analyzer being configured to optically analyze the second light energy to detect an operational condition of the catheter system, the optical analyzer being configured to optically analyze the second light energy to detect at least two of (i) normal operation conditions; (ii) intermittent gas bubble production conditions; (iii) guide distal end plasma initiation conditions; (iv) plasma generation failure conditions; (v) broken light guide conditions; and (vi) chewback conditions.

20. The catheter system of claim 19 wherein upon detection of one or more of plasma generation failure conditions, broken light guide conditions, and chewback conditions, the optical analyzer assembly can be further configured to stop operation of the catheter system.

* * * * *